United States Patent
Kurasawa et al.

(10) Patent No.: US 11,062,111 B2
(45) Date of Patent: Jul. 13, 2021

(54) FINGERPRINT DETECTION DEVICE AND DISPLAY DEVICE

(71) Applicant: Japan Display Inc., Tokyo (JP)

(72) Inventors: Hayato Kurasawa, Tokyo (JP); Yoshitaka Ozeki, Tokyo (JP); Toshinori Uehara, Tokyo (JP); Yuji Suzuki, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 16/831,199

(22) Filed: Mar. 26, 2020

(65) Prior Publication Data

US 2020/0226347 A1 Jul. 16, 2020

Related U.S. Application Data

(63) Continuation of application No. PCT/JP2018/036178, filed on Sep. 28, 2018.

(30) Foreign Application Priority Data

Sep. 29, 2017 (JP) .............................. JP2017-191844

(51) Int. Cl.
G06K 9/00 (2006.01)
(52) U.S. Cl.
CPC ..... *G06K 9/00013* (2013.01); *G06K 9/00067* (2013.01)
(58) Field of Classification Search
None
See application file for complete search history.

(56) References Cited

U.S. PATENT DOCUMENTS

| 6,401,551 | B1 | 6/2002 | Kawahara et al. |
| 2017/0024037 | A1 | 1/2017 | Ishizaki et al. |
| 2017/0123566 | A1* | 5/2017 | Noguchi ............... G06F 3/0445 |

FOREIGN PATENT DOCUMENTS

| JP | 2001-052148 A | 2/2001 |
| JP | 2001-052148 A | 2/2004 |
| JP | 2015-156009 A | 8/2015 |
| JP | 2016-133536 A | 7/2016 |
| JP | 2017-027394 A | 2/2017 |
| JP | 2017-084138 A | 5/2017 |

OTHER PUBLICATIONS

International Search Report and Written Opinion issued in connection with CPT/JP2018/036178, dated Dec. 4, 3029. (4 pages).

* cited by examiner

*Primary Examiner* — Nicholas J Lee
(74) *Attorney, Agent, or Firm* — K&L Gates LLP

(57) ABSTRACT

According to an aspect, a fingerprint detection device includes: a substrate; a plurality of drive electrodes provided on one surface side of the substrate and arranged in a first direction; and a plurality of detection electrodes provided on the one surface side and arranged in a second direction intersecting the first direction. The detection electrodes intersect the drive electrodes in a normal direction of the substrate. Each of the detection electrodes includes: a plurality of first line portions; a plurality of second line portions extending in a direction intersecting the first line portions; and a plurality of bent portions each connecting one of the first line portions and one of the second line portions adjacent to the one of the first line portions to each other.

12 Claims, 21 Drawing Sheets

FINGERPRINT DETECTION DEVICE AND DISPLAY DEVICE

CROSS-REFERENCE TO RELATED APPLICATIONS

This application is a continuation of International Application No. PCT/JP2018/036178, filed on Sep. 28, 2018, which claims priority to Japanese Application No. 2017-191844, filed on Sep. 29, 2017. The contents of these applications are incorporated herein by reference in their entirety.

BACKGROUND

1. Technical Field

The present disclosure relates to a fingerprint detection device and a display device.

2. Description of the Related Art

A display device including a liquid crystal panel or the like may be provided with a fingerprint sensor in some cases. A fingerprint sensor of Japanese Patent Application Laid-open Publication No. 2001-52148 detects a capacitance change corresponding to a recess or protrusion of a fingerprint to detect the shape of a fingerprint of a finger being in contact with the display device. A detection result of the fingerprint sensor is used for personal authentication, for example. The surface of the fingerprint sensor is provided with a cover glass. When a finger is in contact with or proximity to the surface of the cover glass, the fingerprint sensor can detect its fingerprint.

Electrodes in a fingerprint detection region reflect light entering from the cover glass side. When the fingerprint detection region is arranged at a position overlapping with a display region of the display device, the reflection of light by the electrodes in the fingerprint detection region may lead to unintended patterns (e.g., moire and a light reflecting pattern) that can be visually recognized.

For the foregoing reasons, there is a need for a fingerprint detection device and a display device that can reduce the occurrence of unintended patterns.

SUMMARY

According to an aspect, a fingerprint detection device includes: a substrate; a plurality of drive electrodes provided on one surface side of the substrate and arranged in a first direction; and a plurality of detection electrodes provided on the one surface side and arranged in a second direction intersecting the first direction. The detection electrodes intersect the drive electrodes in a normal direction of the substrate. Each of the detection electrodes includes: a plurality of first line portions; a plurality of second line portions extending in a direction intersecting the first line portions; and a plurality of bent portions each connecting one of the first line portions and one of the second line portions adjacent to the one of the first line portions to each other.

According to another aspect, a fingerprint detection device includes: a substrate; a plurality of drive electrodes provided on one surface side of the substrate and arranged in a first direction; and a plurality of detection electrodes provided on the one surface side and arranged in a second direction intersecting the first direction. Each of the drive electrodes includes: a plurality of electrode portions arranged spaced apart from each other in a plan view; and a plurality of connecting portions each connecting adjacent electrode portions of the electrode portions to each other. Each of the electrode portions has a shape including two sides parallel to the drive electrodes. Each of the detection electrodes passes through a gap between the adjacent electrode portions and intersects the connecting portions in a plan view.

According to still another aspect, a display device includes: a display panel; and a fingerprint detection device arranged facing the display panel, the fingerprint detection device including: a substrate; a plurality of drive electrodes provided on one surface side of the substrate and arranged in a first direction; and a plurality of detection electrodes provided on the one surface side and arranged in a second direction intersecting the first direction. The detection electrodes intersect the drive electrodes in a normal direction of the substrate. Each of the detection electrodes includes: a plurality of first line portions; a plurality of second line portions extending in a direction intersecting the first line portions; and a plurality of bent portions each connecting one of the first line portions and one of the second line portions adjacent to the one of the first line portions to each other.

DETAILED DESCRIPTION

Figure 1:
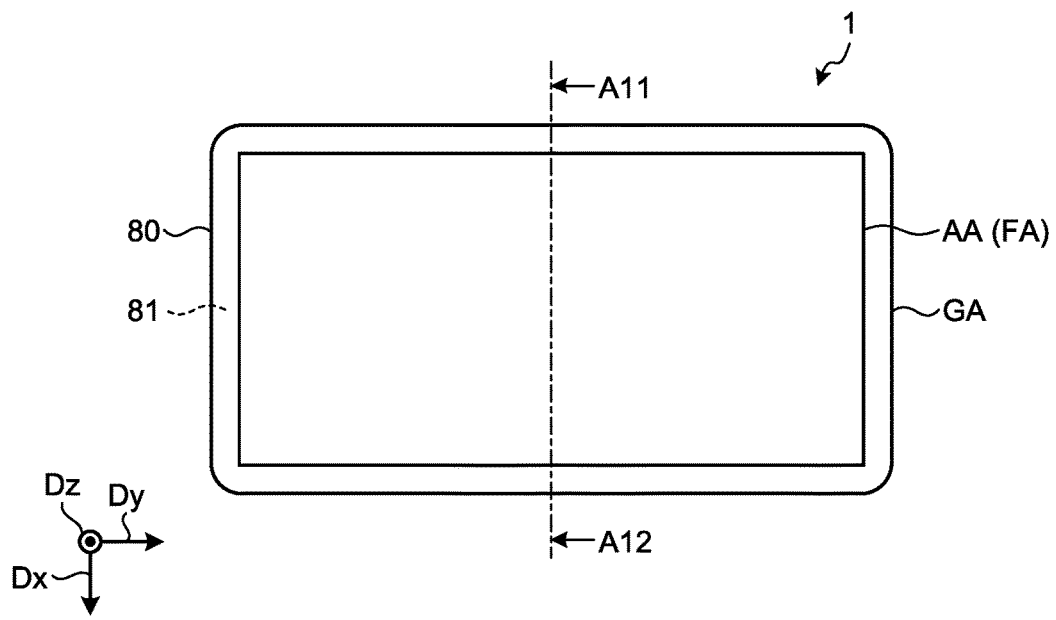
FIG. 1 is a plan view illustrating a display device according to a first embodiment.

Exemplary aspects (embodiments) according to the present disclosure are described below in greater detail with reference to the accompanying drawings. The contents described in the embodiments are not intended to limit the present disclosure. Components described below include components easily conceivable by those skilled in the art and components substantially identical therewith. Furthermore, the components described below can be appropriately combined. The disclosure is given by way of example only, and various changes made without departing from the spirit of the disclosure and easily conceivable by those skilled in the art are naturally included in the scope of the disclosure. The drawings may possibly illustrate the width, the thickness, the shape, and the like of each unit more schematically than the actual aspect to simplify the explanation. These elements, however, are given by way of example only and are not intended to limit interpretation of the present disclosure. In the specification and the drawings, components similar to those previously described with reference to a preceding drawing are denoted by like reference numerals, and detailed explanation thereof will be appropriately omitted. In this disclosure, when an element A is described as being "on" another element B, the element A can be directly on the other element B, or there can be one or more elements between the element A and the other element B.

First Embodiment

Figure 2:
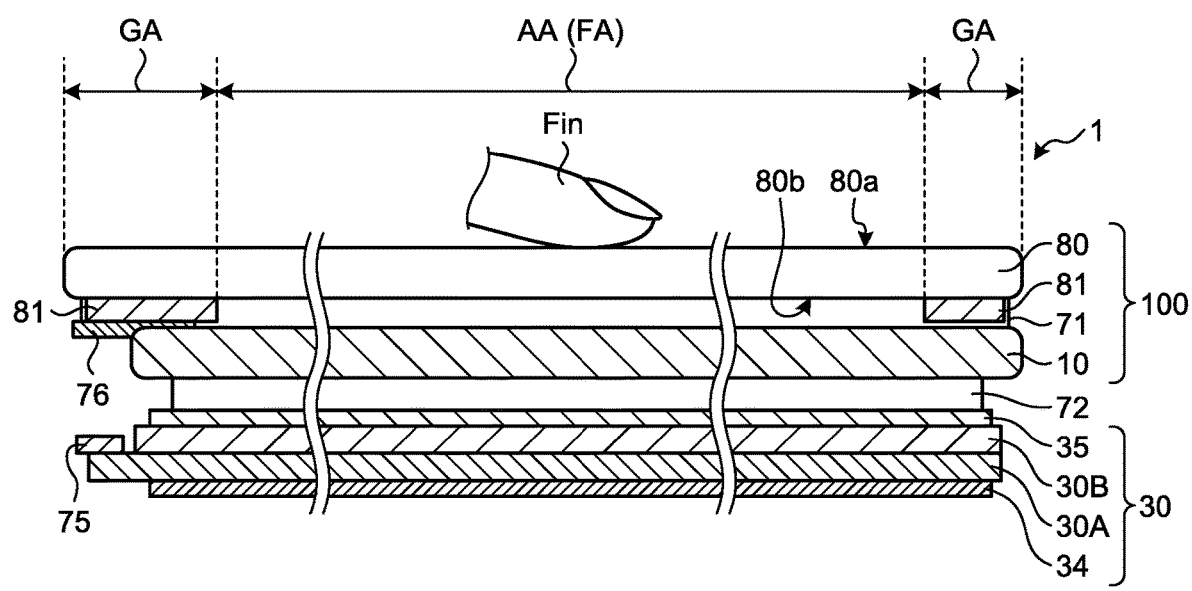
FIG. 2 is a sectional view obtained by cutting the display device illustrated in FIG. 1 along the A11-A12 line.

FIG. 1 is a plan view illustrating a display device according to a first embodiment. FIG. 2 is a sectional view obtained by cutting the display device illustrated in FIG. 1 along the A11-A12 line. The display device 1 illustrated in FIG. 1 is equipped with a fingerprint detection function and includes: a display region AA for displaying an image; a fingerprint detection region FA; and a frame region GA provided outside the display region AA and the fingerprint detection region FA. The fingerprint detection region FA is a region for detecting a recess or protrusion on the surface of a finger or the like being in contact with or in proximity to a cover member 80. In the display device 1 of the present embodiment, the display region AA and the fingerprint detection region FA match with each other or substantially match with each other, thereby enabling detection of a fingerprint across the entire display region AA. The shape of the display region AA and that of the fingerprint detection region FA are rectangular, for example.

As illustrated in FIG. 2, the display device 1 of the present embodiment includes a display panel 30 and a fingerprint detection device 100. The fingerprint detection device 100 has a fingerprint sensor 10 and the cover member 80. The cover member 80 is a plate-shaped member having a first surface 80a and a second surface 80b on the side opposite of the first surface 80a. The first surface 80a of the cover member 80 is a detection surface for detecting the recess or protrusion on the surface of the finger or the like being in contact therewith or in proximity thereto, and is also a display surface for allowing an observer to visually recognize an image on the display panel 30. The fingerprint sensor 10 and the display panel 30 are provided on the second surface 80b side of the cover member 80. The cover member 80 is a member for protecting the fingerprint sensor 10 and the display panel 30 and covers the fingerprint sensor 10 and the display panel 30. The cover member 80 is a glass substrate or a resin substrate, for example.

The shapes of the cover member 80, the fingerprint sensor 10, and the display panel 30 are not limited to be rectangular in a plan view, and may be circular, oval, or an odd shape with part of these outer shape lacked. The shape of the cover member 80 is not limited to be plate-shaped. When the display region AA and the fingerprint detection region FA each have a curved surface or the frame region GA has a curved surface curving toward the display panel 30, for example, the cover member 80 may have a curved surface. In this case, the display device is a curved surface display having a fingerprint detection function and can detect a fingerprint also on the curved surface of the curved surface display. A "plan view" indicates a case when viewed from a direction perpendicular to one surface 101a of a substrate 101 illustrated in FIG. 3 described below. The direction perpendicular to the one surface 101a is a "normal direction Dz of the substrate 101".

As illustrated in FIG. 1 and FIG. 2, in the frame region GA, a decorative layer 81 is provided on the second surface 80b of the cover member 80. The decorative layer 81 is a coloring layer, light transmittance of which is lower than that of the cover member 80. The decorative layer 81 can prevent wiring, circuits, and the like provided superimposed on the frame region GA from being visually recognized by the observer. In the example illustrated in FIG. 2, the decorative layer 81 is provided on the second surface 80b, but it may be provided on the first surface 80a. The decorative layer 81 is not limited to be a single layer and may have a multilayered configuration.

The fingerprint sensor 10 is a detector for detecting a recess or protrusion on the surface of a finger Fin or the like being in contact with or in proximity to the first surface 80a of the cover member 80. As illustrated in FIG. 2, the fingerprint sensor 10 is provided between the cover member 80 and the display panel 30. When viewed from a direction perpendicular to the first surface 80a (normal direction), the fingerprint sensor 10 overlaps with the fingerprint detection region FA and part of the frame region GA. A flexible substrate 76 is connected to the fingerprint sensor 10 in the frame region GA. An integrated circuit (IC) for detection (not illustrated) for controlling detection operations of the fingerprint sensor 10 is mounted on the flexible substrate 76.

One surface of the fingerprint sensor 10 is stuck to the second surface 80b of the cover member 80 with an adhesive layer 71, whereas the other surface thereof is stuck to a polarizing plate 35 of the display panel 30 with an adhesive layer 72. Each of the adhesive layer 71 and the adhesive layer 72 is an adhesive or a resin having translucency, and allows visible light to pass therethrough.

The display panel 30 includes: a pixel substrate 30A; a counter substrate 30B; a polarizing plate 34 provided below the pixel substrate 30A; and the polarizing plate 35 provided above the counter substrate 30B. An IC for display (not illustrated) for controlling a display operation of the display panel 30 is connected to the pixel substrate 30A via a flexible substrate 75. In the present embodiment, the display panel 30 is a liquid crystal panel, in which a liquid crystal element is used as a display function layer. However, the present disclosure is not limited to this example, and the display panel 30 may be an organic EL display panel, for example. The IC for detection and the IC for display described above may be provided on a control substrate outside a module. Alternatively, the IC for detection may be provided on the substrate 101 of the fingerprint sensor 10 (refer to FIG. 3 and FIG. 14). The IC for display may be provided on a first substrate 31 of the pixel substrate 30A (refer to FIG. 8).

Figure 3:
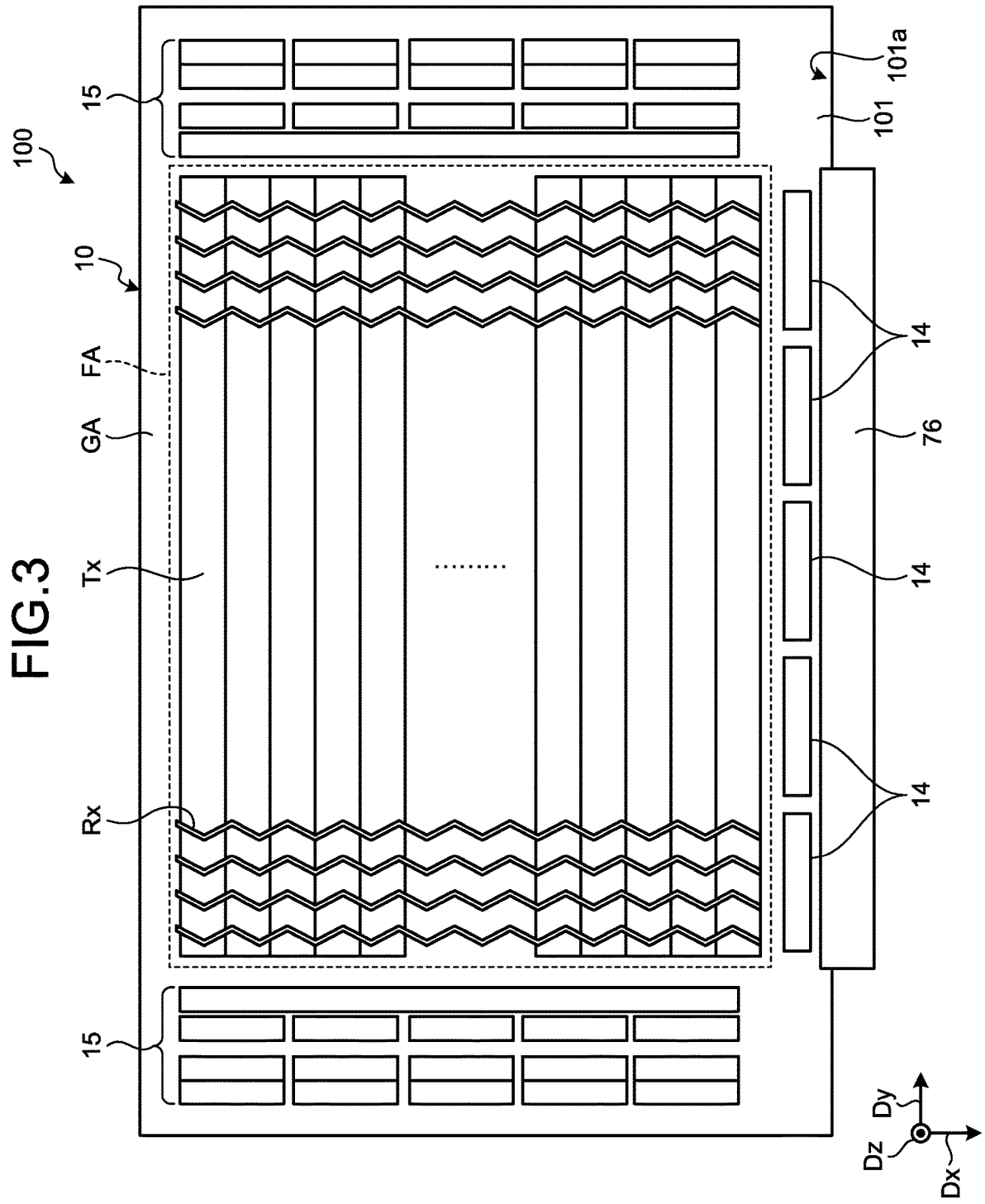
FIG. 3 is a plan view illustrating a configuration example of a fingerprint detection device according to the first embodiment.

FIG. 3 is a plan view illustrating a configuration example of the fingerprint detection device according to the first embodiment. As illustrated in FIG. 3, the fingerprint detection device 100 includes the substrate 101 and the fingerprint sensor 10 provided on the one surface 101a side of the substrate 101. The fingerprint sensor 10 includes drive electrodes Tx and detection electrodes Rx provided on the one surface 101a side of the substrate 101. The substrate 101 is a glass substrate having translucency allowing visible light to pass therethrough. The substrate 101 may be a translucent resin substrate or a resin film formed of a resin such as polyimide. The fingerprint sensor 10 is a sensor having translucency. The drive electrodes Tx are formed of a translucent conductive material such as indium tin oxide (ITO).

The drive electrodes Tx are arranged in a first direction Dx. The drive electrodes Tx extend in a second direction Dy. The detection electrodes Rx are arranged in the second direction Dy. The detection electrodes Rx extend in the first direction Dx. In this manner, the detection electrodes Rx extend in a direction intersecting the extension direction of the drive electrodes Tx. The detection electrodes Rx are each connected to the flexible substrate 75 provided on a short side of the frame region GA of the substrate 101 via frame wiring (not illustrated). In the present embodiment, the drive electrodes Tx employs a conductive material having translucency such as ITO. As illustrated in FIG. 3, the drive electrodes Tx and the detection electrodes Rx are provided in the fingerprint detection region FA.

Capacitance is formed at each of intersections between the detection electrodes Rx and the drive electrodes Tx. When a mutual capacitance touch detection operation is performed in the fingerprint sensor 10, a drive electrode driver 15 sequentially selects the drive electrodes Tx in a time division manner, and supplies a drive signal Vs to the selected drive electrode Tx. A detection signal Vdet corresponding to a capacitance change by the recess or protrusion on the surface of the finger or the like being in contact with or in proximity to the cover member 80 is output from the detection electrodes Rx, whereby fingerprint detection is performed. The drive electrode driver 15 may sequentially select each drive electrode block including a plurality of drive electrodes Tx and drive the drive electrodes Tx.

While FIG. 3 illustrates a case in which the various kinds of circuits such as a detection electrode selection circuit 14 and the drive electrode driver 15 are provided in the frame region GA of the substrate 101, this is a mere example. At least part of the various kinds of circuits may be included in the IC for detection mounted on the flexible substrate 76.

Figure 4:
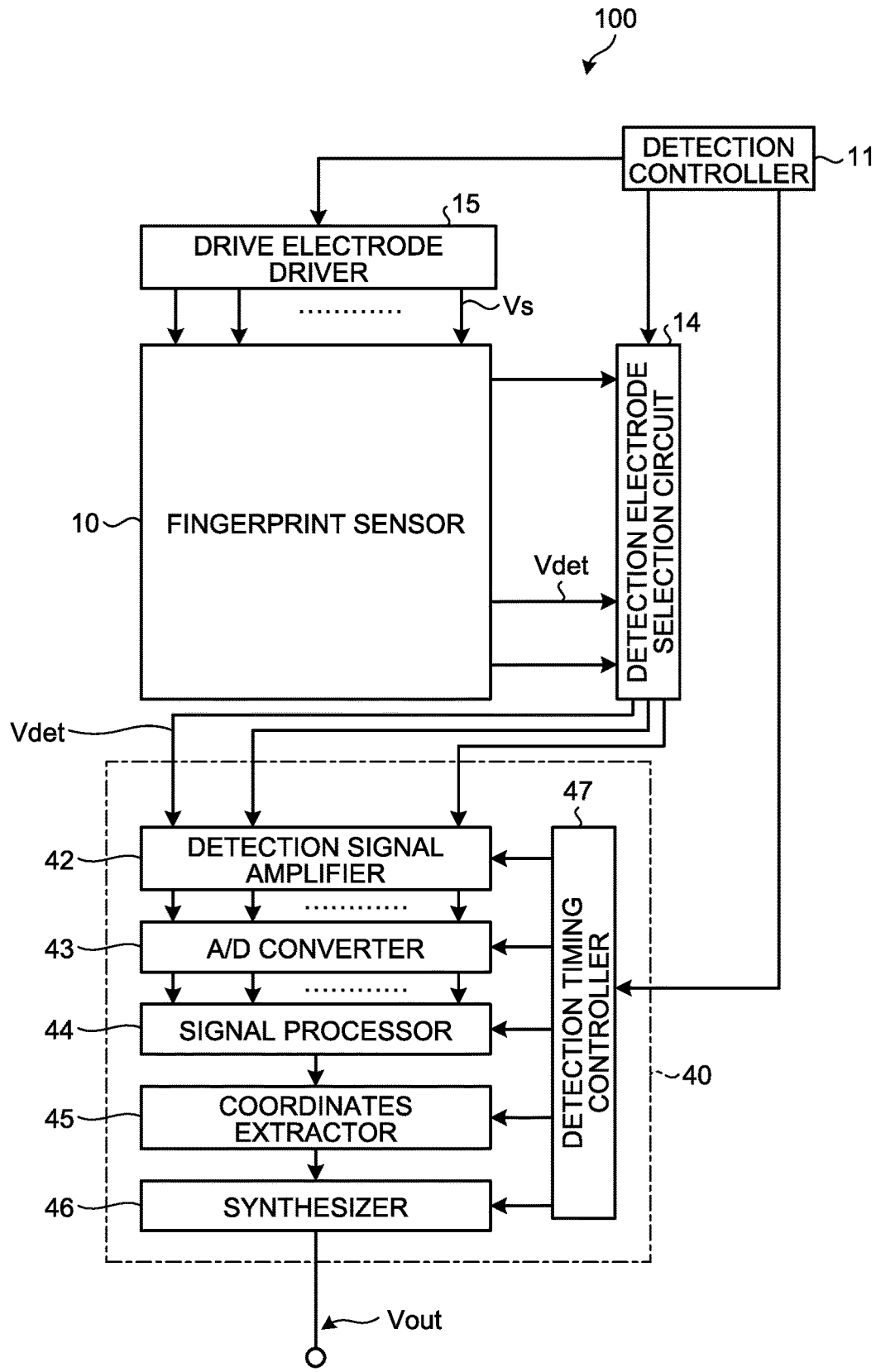
FIG. 4 is a block diagram illustrating a configuration example of the fingerprint detection device.

The following describes a detailed configuration of the fingerprint detection device. FIG. 4 is a block diagram illustrating a configuration example of the fingerprint detection device including the fingerprint sensor. As illustrated in FIG. 4, the fingerprint detection device 100 includes the fingerprint sensor 10, a detection controller 11, the drive electrode driver 15, the detection electrode selection circuit 14, and a detector 40.

The detection controller 11 is a circuit for controlling detection operations of the fingerprint sensor 10. The drive electrode driver 15 is a circuit for supplying a drive signal Vs for detection to the drive electrodes Tx of the fingerprint sensor 10 based on a control signal supplied from the detection controller 11. The detection electrode selection circuit 14 selects the detection electrodes Rx of the fingerprint sensor 10 based on a control signal supplied from the detection controller 11 to connect the selected detection electrodes Rx to the detector 40.

The detector 40 is a circuit for detecting the recess or protrusion on the surface of the finger or the like being in contact with or in proximity to the first surface 80a of the cover member 80 based on a control signal supplied from the detection controller 11 and the detection signal Vdet output from the detection electrodes Rx to detect the shape of a fingerprint. The detector 40 includes a detection signal amplifier 42, an analog-to-digital (A/D) converter 43, a signal processor 44, a coordinates extractor 45, a synthesizer 46, and a detection timing controller 47. The detection timing controller 47 performs control to cause the detection signal amplifier 42, the A/D converter 43, the signal processor 44, the coordinates extractor 45, and the synthesizer 46 to operate in synchronization with each other based on a control signal supplied from the detection controller 11.

The detection signal Vdet is supplied to the detection signal amplifier 42 of the detector 40 from the fingerprint sensor 10. The detection signal amplifier 42 amplifies the detection signal Vdet. The A/D converter 43 converts an analog signal output from the detection signal amplifier 42 into a digital signal.

The signal processor 44 is a logic circuit for detecting whether the finger is in contact with or in proximity to the fingerprint sensor 10 based on an output signal of the A/D converter 43. The signal processor 44 performs processing to extract a differential signal of detection signals (an absolute value $|\Delta V|$) generated by the finger. The signal processor 44 compares the absolute value $|\Delta V|$ with a certain threshold voltage. If this absolute value $|\Delta V|$ is less than the threshold voltage, the signal processor determines that the finger is in a non-contact state. On the other hand, if the absolute value $|\Delta V|$ is the threshold voltage or greater, the signal processor 44 determines that the finger is in a contact-or-proximity state. In this manner, the detector 40 can detect the contact or proximity of the finger.

The coordinates extractor 45 is a logic circuit that, when the contact or proximity of the finger is detected by the signal processor 44, determines its detected coordinates. The coordinates extractor 45 outputs the detected coordinates to the synthesizer 46. The synthesizer 46 combines the detection signal Vdet output from the fingerprint sensor 10 to generate two-dimensional information indicating the shape of the finger being in contact with or in proximity to the fingerprint sensor 10. The synthesizer 46 outputs the two-dimensional information as output Vout of the detector 40. Alternatively, the synthesizer 46 may generate an image based on the two-dimensional information and make image information serve as the output Vout.

The IC for detection described above functions as the detector 40 illustrated in FIG. 4. Part of the functions of the detector 40 may be included in the IC for display described above or be provided as functions of an external microprocessing unit (MPU).

Figure 5:
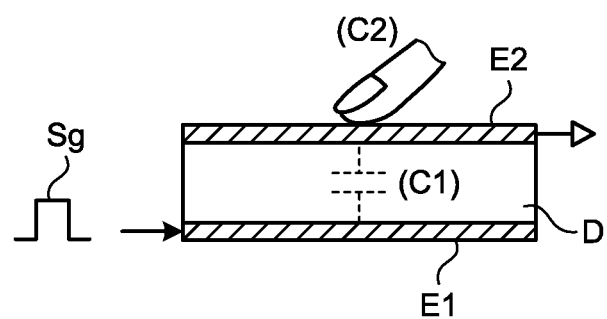
FIG. 5 is a diagram for explaining the basic principle of mutual capacitance detection.
Figure 6:
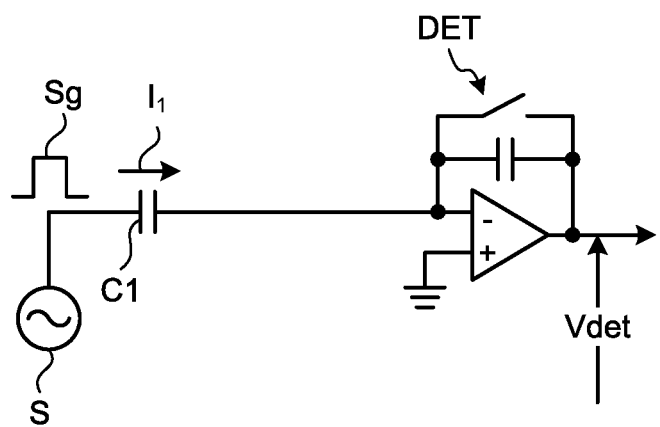
FIG. 6 is a diagram illustrating an exemplary equivalent circuit for explaining the basic principle of the mutual capacitance detection.
Figure 7:
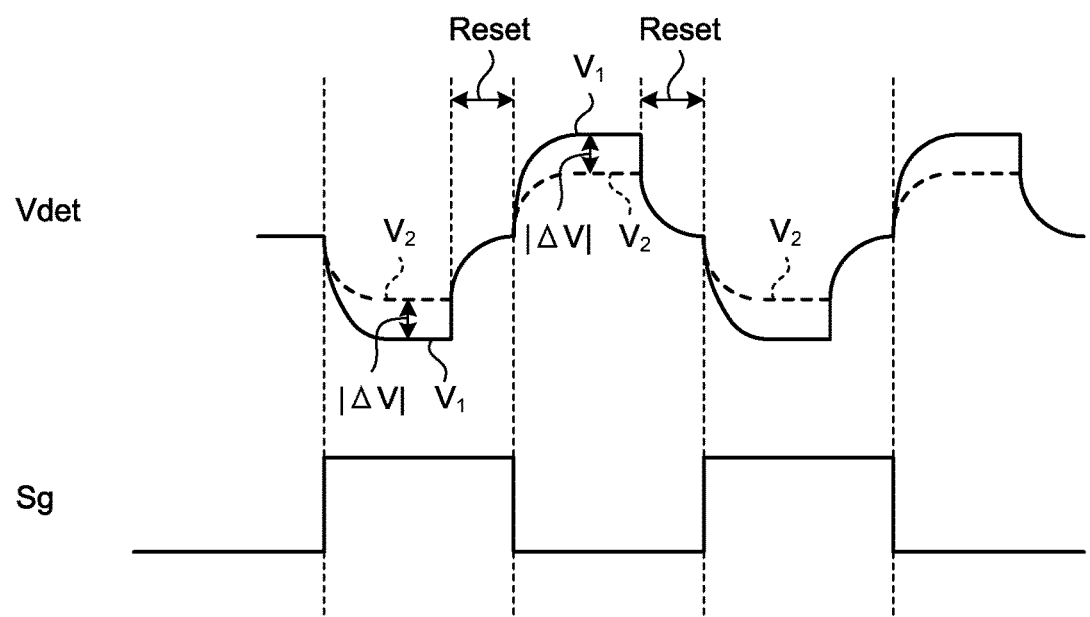
FIG. 7 is a diagram illustrating exemplary waveforms of a drive signal and a detection signal of the mutual capacitance detection.

The fingerprint sensor 10 operates based on the basic principle of capacitance type detection. The following describes the basic principle of mutual capacitance detection by the fingerprint sensor 10 with reference to FIG. 5 to FIG. 7. FIG. 5 is a diagram for explaining the basic principle of mutual capacitance detection. FIG. 6 is a diagram illustrating an exemplary equivalent circuit for explaining the basic principle of the mutual capacitance detection. FIG. 7 is a diagram illustrating exemplary waveforms of a drive signal and a detection signal of the mutual capacitance detection. While the following describes a case in which a finger is in contact with or in proximity to a detection electrode, the present disclosure is not limited to the finger, and a target may be an object including a conductor such as a stylus, for example.

As illustrated in FIG. 5, for example, a capacitance element C1 includes a pair of electrodes facing each other across a dielectric D, i.e., a drive electrode E1 and a detection electrode E2. The capacitance element C1 produces lines of electric force for a fringe extending from ends of the drive electrode E1 toward an upper surface of the detection electrode E2 in addition to lines of electric force (not illustrated) generated between opposing surfaces of the drive electrode E1 and the detection electrode E2. As illustrated in FIG. 6, one end of the capacitance element C1 is connected to an AC signal source (a drive signal source) S, whereas the other end thereof is connected to a voltage detector DET. The voltage detector DET is an integral circuit included in the detector 40 illustrated in FIG. 4, for example.

When the AC signal source S applies an AC rectangular wave Sg at a predetermined frequency (e.g., a frequency of several kilohertz to several hundred kilohertz) to the drive electrode E1 (one end of the capacitance element C1), an output waveform (the detection signal Vdet) as illustrated in FIG. 7 appears via the voltage detector DET connected to the detection electrode E2 (the other end of the capacitance element C1). The AC rectangular wave Sg corresponds to the drive signal Vs input from the drive electrode driver 15 illustrated in FIG. 4.

In a state in which the finger is not in contact with or in proximity to the detection electrode E2 (non-contact state), a current corresponding to the capacitance value of the capacitance element C1 flows with charge and discharge of the capacitance element C1. The voltage detector DET illustrated in FIG. 6 converts fluctuations in a current $I_1$ corresponding to the AC rectangular wave Sg into fluctuations in voltage (a solid line waveform $V_1$ (refer to FIG. 7)).

On the other hand, in a state in which the finger is in contact with or proximity to the detection electrode E2 (contact state), as illustrated in FIG. 5, capacitance C2 generated by the finger is in contact with or near the detection electrode E2. With this configuration, the lines of electric force for a fringe between the drive electrode E1 and the detection electrode E2 are blocked by the conductor (the finger). Consequently, the capacitance element C1 acts as a capacitance element with a capacitance value smaller than a capacitance value in the non-contact state. As illustrated in FIG. 6 and FIG. 7, the voltage detector DET converts the fluctuations in the current $I_1$ corresponding to the AC rectangular wave Sg into fluctuations in voltage (a dotted line waveform $V_2$).

In this case, the waveform $V_2$ is smaller in amplitude than the waveform $V_1$ described above. With this relation, the absolute value $|\Delta V|$ of a voltage difference between the waveform $V_1$ and the waveform $V_2$ changes in accordance with the influence of an external object being in contact with or in proximity to the detection electrode E2 from the outside such as a finger. In order for the voltage detector DET to accurately detect the absolute value $|\Delta V|$ of the voltage difference between the waveform $V_1$ and the waveform $V_2$, the voltage detector DET preferably operates with a period Reset to reset charge and discharge of a capacitor in accordance with the frequency of the AC rectangular wave Sg by switching in the circuit.

The detector 40 compares the absolute value $|\Delta V|$ with a certain threshold voltage. If the absolute value $|\Delta V|$ is less than the threshold voltage, the detector 40 determines that the finger is in the non-contact state. On the other hand, if the absolute value $|\Delta V|$ is the threshold voltage or greater, the detector 40 determines that the finger is in the contact-or-proximity state. When it is determined that the finger is in the contact-or-proximity state, the detector 40 detects a capacitance change by the recess or protrusion on the surface of the finger based on a difference in the absolute value $|\Delta V|$. The drive electrode E1 illustrated in FIG. 5 corresponds to the drive electrode Tx illustrated in FIG. 3, whereas the detection electrode E2 illustrated in FIG. 5 corresponds to the detection electrode Rx illustrated in FIG. 3.

Figure 8:
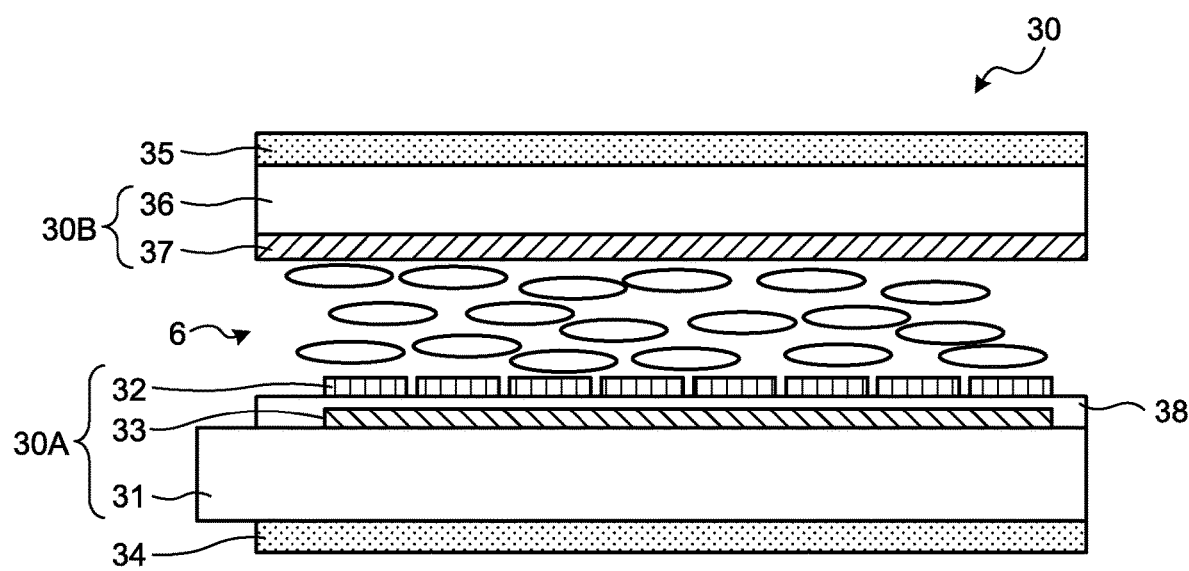
FIG. 8 is a sectional view illustrating a configuration example of a display panel.

FIG. 8 is a sectional view illustrating a configuration example of a display panel. The pixel substrate 30A includes a first substrate 31, pixel electrodes 32, and a common electrode 33. The common electrode 33 is provided on the first substrate 31. The pixel electrodes 32 are provided above the common electrode 33 via an insulating layer 38, and are arranged in a matrix (row-column configuration) in a plan view. The pixel electrodes 32 are provided corresponding to respective subpixels forming each pixel Pix of the display panel 30, and are supplied with pixel signals for performing a display operation. The common electrode 33, to which DC drive signals for display are supplied, functions as a common electrode for the pixel electrodes 32.

In the present embodiment, the common electrode 33, the insulating layer 38, and the pixel electrodes 32 are stacked in this order on the first substrate 31. The polarizing plate 34 is provided below the first substrate 31 via an adhesive layer. Thin film transistors (TFT, not illustrated) serving as switching elements for display are provided to the first substrate 31. For example, a conductive material having translucency such as ITO is used for the pixel electrodes 32 and the common electrode 33.

The arrangement of the pixel electrodes 32 is not limited to the matrix arrangement in which the pixel electrodes 32 are arranged in a first direction and a second direction orthogonal to the first direction, and may employ an arrangement in which adjacent pixel electrodes 32 are shifted from each other in the first direction or the second direction. Alternatively, the present disclosure can employ a configuration in which, with respect to one pixel electrode 32 constituting a pixel column in the first direction, two or three pixel electrodes 32 are arranged on one side of the one pixel electrode 32, according to a difference in shape between adjacent pixel electrodes 32.

The counter substrate 30B includes a second substrate 36 and a color filter 37 formed on one surface of the second substrate 36. The color filter 37 faces a liquid crystal layer 6 in a direction perpendicular to the first substrate 31. Further, the polarizing plate 35 is provided above the second substrate 36 via an adhesive layer. The color filter 37 may be arranged on the first substrate 31. In the present embodiment, each of the first substrate 31 and the second substrate 36 is a glass substrate or a resin substrate, for example.

The liquid crystal layer 6 is provided between the first substrate 31 and the second substrate 36. The liquid crystal layer 6 modulates light passing therethrough in accordance with the state of an electric field, and employs liquid crystals in a transverse electric field mode such as an in-plane switching (IPS) mode including a fringe field switching (FFS) mode. An orientation film may be provided between the liquid crystal layer 6 and the pixel substrate 30A and between the liquid crystal layer 6 and the counter substrate 30B illustrated in FIG. 8.

An illuminator (a backlight, not illustrated) is provided below the first substrate 31. The illuminator has a light source such as a light-emitting diode (LED), for example, and emits light from the light source toward the first substrate 31. The light from the illuminator passes through the pixel substrate 30A, and switching is performed between part of the light to be blocked and not to be emitted and part of the light to be emitted depending on the state of liquid crystals, so that an image is displayed on the display surface (the first surface 80a).

As illustrated in FIG. 2, the display panel 30 is stuck to the fingerprint sensor 10 via the adhesive layer 72 provided on the polarizing plate 35 in the display region AA. The fingerprint sensor 10 is arranged at a position closer to the cover member 80 than the display panel 30 is to the cover member 80 in a direction orthogonal to the second surface 80b of the cover member 80. The provision of the fingerprint sensor 10 closer to the cover member 80 can reduce a distance between the detection electrodes Rx and the first surface 80a serving as the detection surface, in comparison with a case in which detection electrodes for fingerprint detection are provided integrally with the display panel 30, for example. Consequently, the display device 1 of the present embodiment can improve detection performance.

Figure 9:
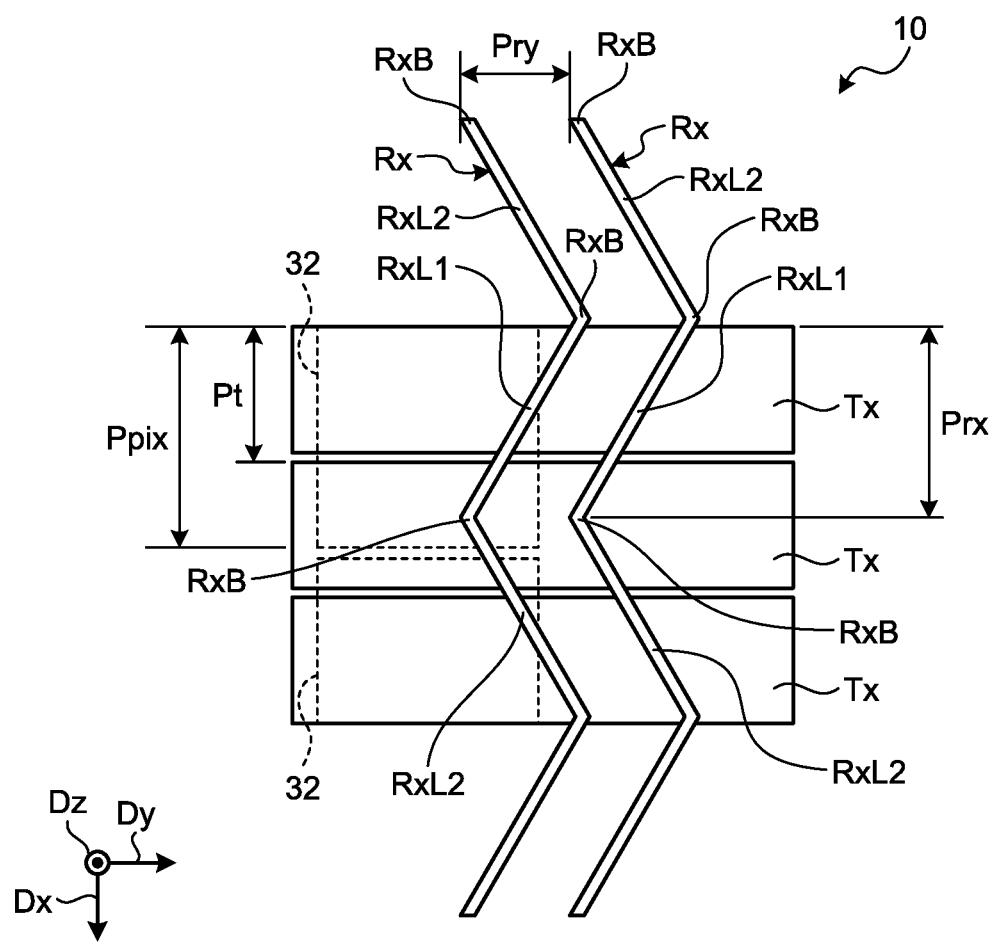
FIG. 9 is a plan view illustrating a configuration example of a fingerprint sensor according to the first embodiment.

FIG. 9 is a plan view illustrating a configuration example of detection electrodes of the fingerprint sensor according to the first embodiment. As illustrated in FIG. 9, the detection electrodes Rx intersect the drive electrodes Tx. When viewed from the normal direction Dz, the shape of the detection electrode Rx is a zigzag line. The detection electrodes Rx zigzag in the first direction Dx. The detection electrodes Rx each have a plurality of first line portions RxL1, a plurality of second line portions RxL2, and a plurality of bent portions RxB, for example. The second line portions RxL2 extend in a direction intersecting the first line portions RxL1. The bent portions RxB connect the first line portions RxL1 and the second line portions RxL2 to each other.

For example, the first line portions RxL1 extend in a direction intersecting the first direction Dx and the second direction Dy. The second line portions RxL2 also extend in a direction intersecting the first direction Dx and the second direction Dy. The first line portions RxL1 and the second line portions RxL2 are arranged so as to be bilaterally symmetric about a virtual line (not illustrated) parallel to the first direction Dx.

In each of the detection electrodes Rx, an arrangement pitch of bent portions RxB in the first direction Dx is defined as Prx. In adjacent detection electrodes Rx, an arrangement pitch of the bent portions RxB in the second direction Dy is defined as Pry. In the present embodiment, a magnitude relation of Pry<Prx holds, for example.

An arrangement pitch of the drive electrodes Tx in the first direction Dx is defined as Pt. An arrangement pitch in the first direction Dx of the pixel electrodes 32 of the display panel 30 stuck to the fingerprint detection device 100 is defined as Ppix. In the present embodiment, a magnitude relation of the arrangement pitch Pt of the drive electrodes Tx and the arrangement pitch Ppix of the pixel electrodes 32 preferably satisfies the following Expression (1), where n is an integer of 1 or more. With this relation, the fingerprint sensor 10 can reduce the occurrence of unintended patterns (e.g., moire and a light reflecting pattern) in the fingerprint detection region FA.

$$0.6 \times (n-1) \times Ppix \leq Pt \leq 0.4 \times n \times Ppix \quad (1)$$

Figure 10:
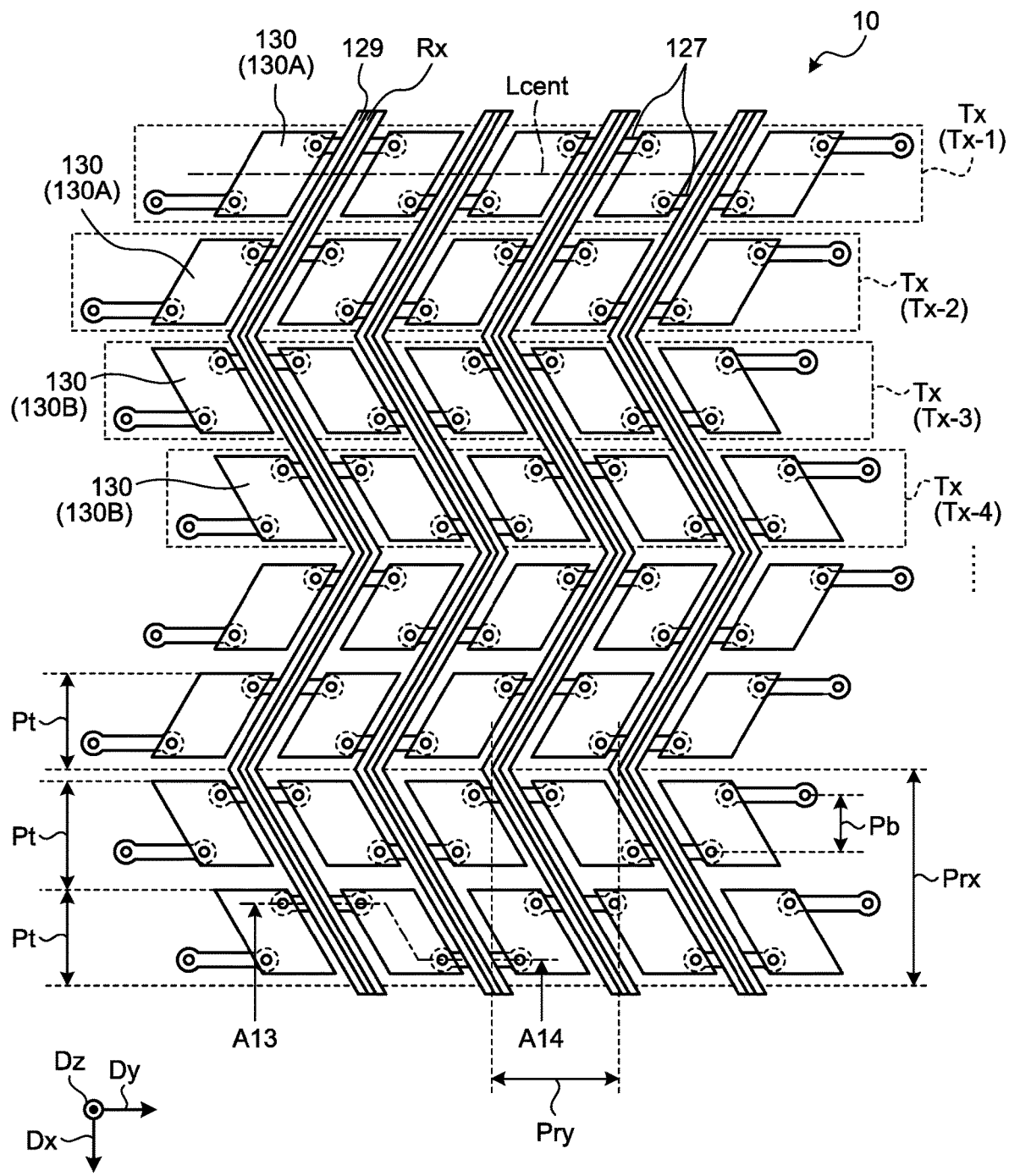
FIG. 10 is a plan view illustrating a configuration example of drive electrodes according to the first embodiment.

The following describes the shape of the drive electrodes Tx more specifically. FIG. 10 is a plan view illustrating a configuration example of the drive electrodes according to the first embodiment. As illustrated in FIG. 10, the drive electrodes Tx (e.g., TX-1, TX-2, TX-3, TX-4, . . . ) arranged in the first direction Dx each have a plurality of electrode portions 130 and a plurality of connecting portions 127. In each of the drive electrodes Tx, the electrode portions 130 are arranged in the second direction Dy and are arranged spaced apart from each other. In each of the drive electrodes Tx, the connecting portion 127 connects adjacent electrode portions among the electrode portions 130 to each other. As illustrated in FIG. 10, when viewed from the normal direction Dz of the substrate 101 (refer to FIG. 3), one detection electrode Rx passes through a gap between adjacent electrode portions 130 and intersects the connecting portions 127.

An arrangement pitch of the connecting portions 127 in the first direction Dx is defined as Pb. The arrangement pitch Pb of the connecting portions 127 is preferably 0.5 times the arrangement pitch Pt of the drive electrode Tx. In each of the drive electrodes Tx, the connecting portions 127 are preferably arranged alternately on one side and the other side relative to a virtual line Lcent parallel to the second direction Dy and passing through the center of gravity of the electrode portions 130. With this structure, the connecting portions 127, light transmittance of which is lower than that of the electrode portions 130, are not arranged on a straight line, so that the fingerprint sensor 10 can reduce the occurrence of unintended patterns such as moire.

The longitudinal directions of the connecting portions 127 are preferably aligned in one direction. All of the longitudinal directions of the connecting portions 127 of the drive electrodes Tx are the second direction, for example. This structure uniforms the shape of the connecting portions 127 intersecting the detection electrodes Rx, which makes it easy to uniform capacitance between the drive electrodes Tx and the connecting portions 127.

In the fingerprint sensor 10 illustrated in FIG. 10, the shape of the drive electrodes Tx, the shape of the detection electrodes Rx, and the positional relation thereof are uniform among the electrode portions, and thus variations in capacitance of the drive electrodes Tx and variations in capacitance of the detection electrodes Rx are small. Further, there is an advantage that the calculation of coordinates in the fingerprint sensor 10 is easily corrected, for example.

Figure 11:
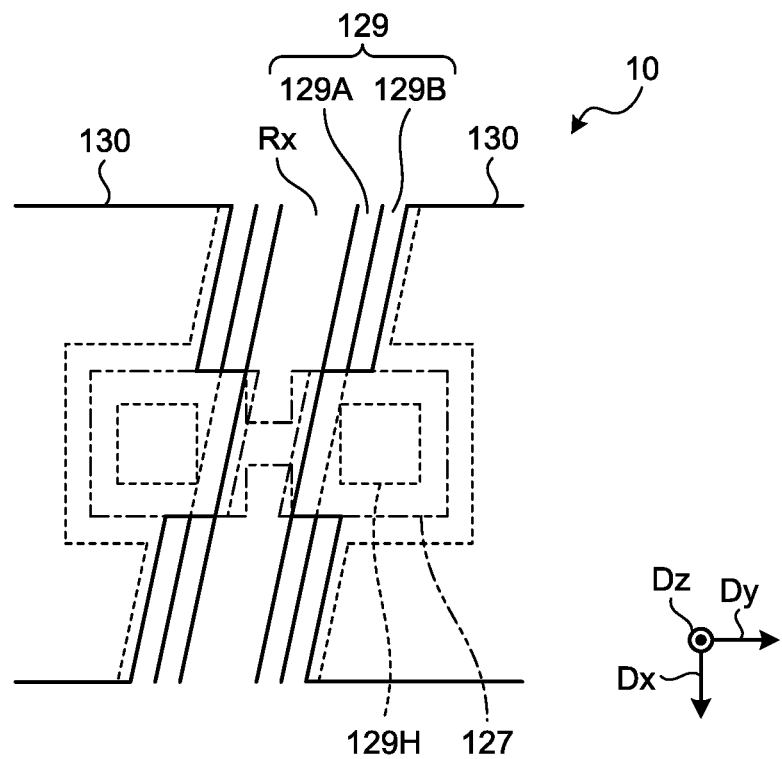
FIG. 11 is a plan view illustrating a drive electrode and a detection electrode according to the first embodiment.
Figure 12:
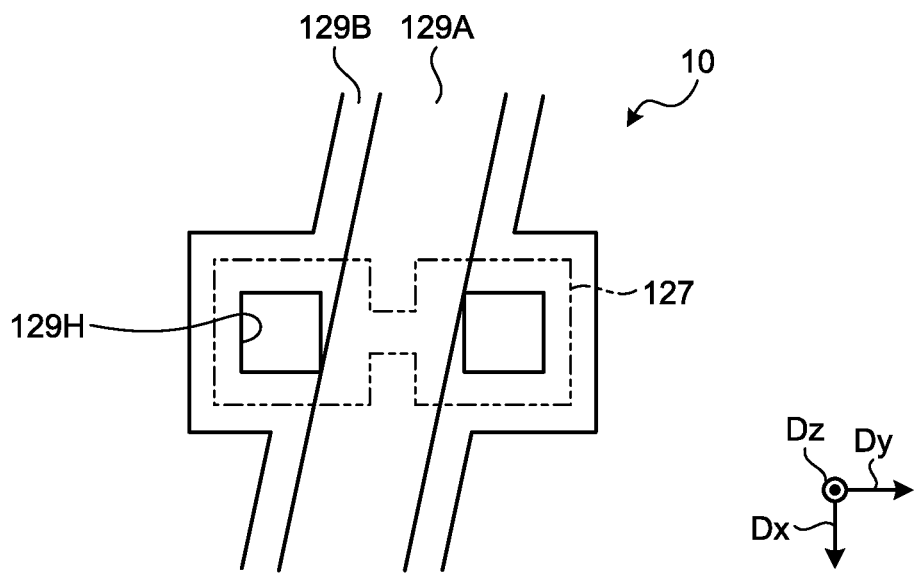
FIG. 12 is a diagram omitting the illustration of electrode portions and the detection electrode in FIG. 11.

FIG. 11 is a plan view illustrating a drive electrode and a detection electrode according to the first embodiment. FIG. 12 is a diagram omitting the illustration of the electrode portions and the detection electrode in FIG. 11. As illustrated in FIG. 11, an insulating film 129 is arranged between the connecting portion 127 and the detection electrode Rx. The insulating film 129 is a resin insulating film, for example. The insulating film 129 includes a first insulating film 129A and a second insulating film 129B thinner than the first insulating film 129A. The second insulating film 129B is provided with a contact hole 129H. As illustrated in FIG. 12, the connecting portion 127 is exposed at the bottom of the contact hole 129H.

Figure 13:
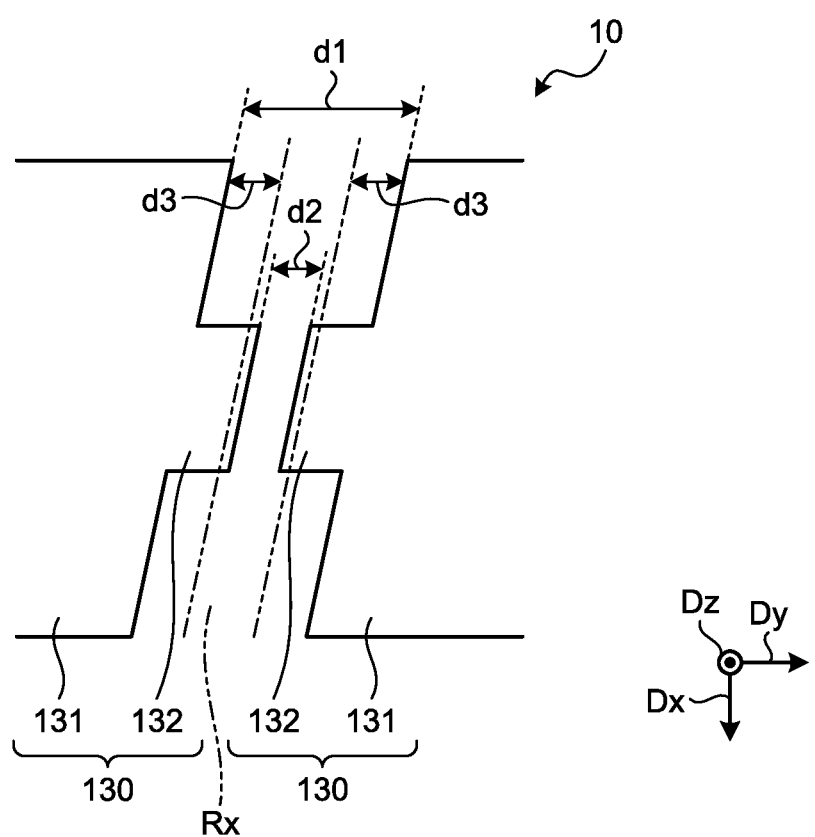
FIG. 13 is a plan view illustrating a configuration example of the electrode portions.

FIG. 13 is a plan view illustrating a configuration example of the electrode portions. As illustrated in FIG. 13, the electrode portion 130 has an electrode main body 131 and a protruding portion 132 in a plan view protruding toward an adjacent electrode portion 130 from the electrode main body 131. The second insulating film 129B is arranged between the protruding portion 132 and the connecting portion 127. The protruding portion 132 is embedded in the contact hole 129H (refer to FIG. 11) provided in the second insulating film 129B. With this structure, the protruding portion 132 is connected to the connecting portion 127 (refer to FIG. 11) via the contact hole 129H. The electrode portions 130 are connected to each other in the second direction Dy via the connecting portions 127.

In the second direction Dy, when a distance between adjacent electrode main bodies 131 is defined as d1, and a distance between adjacent protruding portions 132 is defined as d2, a magnitude relation of d1>d2 holds. When viewed from the normal direction Dz, the detection electrode Rx is arranged so as to overlap with the protruding portions 132 and capacitance generated between the electrode portions 130 and the detection electrode Rx can be reduced, in comparison with a case in which the electrode main bodies 131 and the detection electrode Rx overlap with each other.

As illustrated in FIG. 10, when viewed from the normal direction Dz, the electrode portions 130 have a plurality of shapes. For example, the electrode portions 130 include a first electrode portion 130A and a second electrode portion 130B, the shape of the electrode main body 131 (refer to FIG. 13) of which is different from that of the first electrode portion 130A. When viewed from the normal direction Dz, each of the shape of the electrode main body 131 of the first electrode portion 130A and the shape of the electrode main body 131 of the second electrode portion 130B is a parallelogram. When viewed from the normal direction Dz, the shape of the electrode main body 131 of the first electrode portion 130B is obtained by vertically flipping the shape of the electrode main body 131 of the second electrode portion 130A.

For example, the drive electrodes Tx-1 and Tx-2 intersecting the first line portions RxL1 of the detection electrodes Rx (refer to FIG. 9) include the first electrode portion 130A having two sides parallel to the first line portions RxL1. The drive electrodes Tx-3 and Tx-4 intersecting the second line portions RxL2 of the detection electrodes Rx (refer to FIG. 9) include the second electrode portion 130B having two sides parallel to the second line portions RxL2. With this structure, when viewed from the normal direction Dz, the electrode main bodies 131 can be arranged along the zigzag detection electrode Rx, and a separating distance d3 between the zigzag detection electrode Rx and the electrode main bodies 131 can be a constant length.

Figure 14:
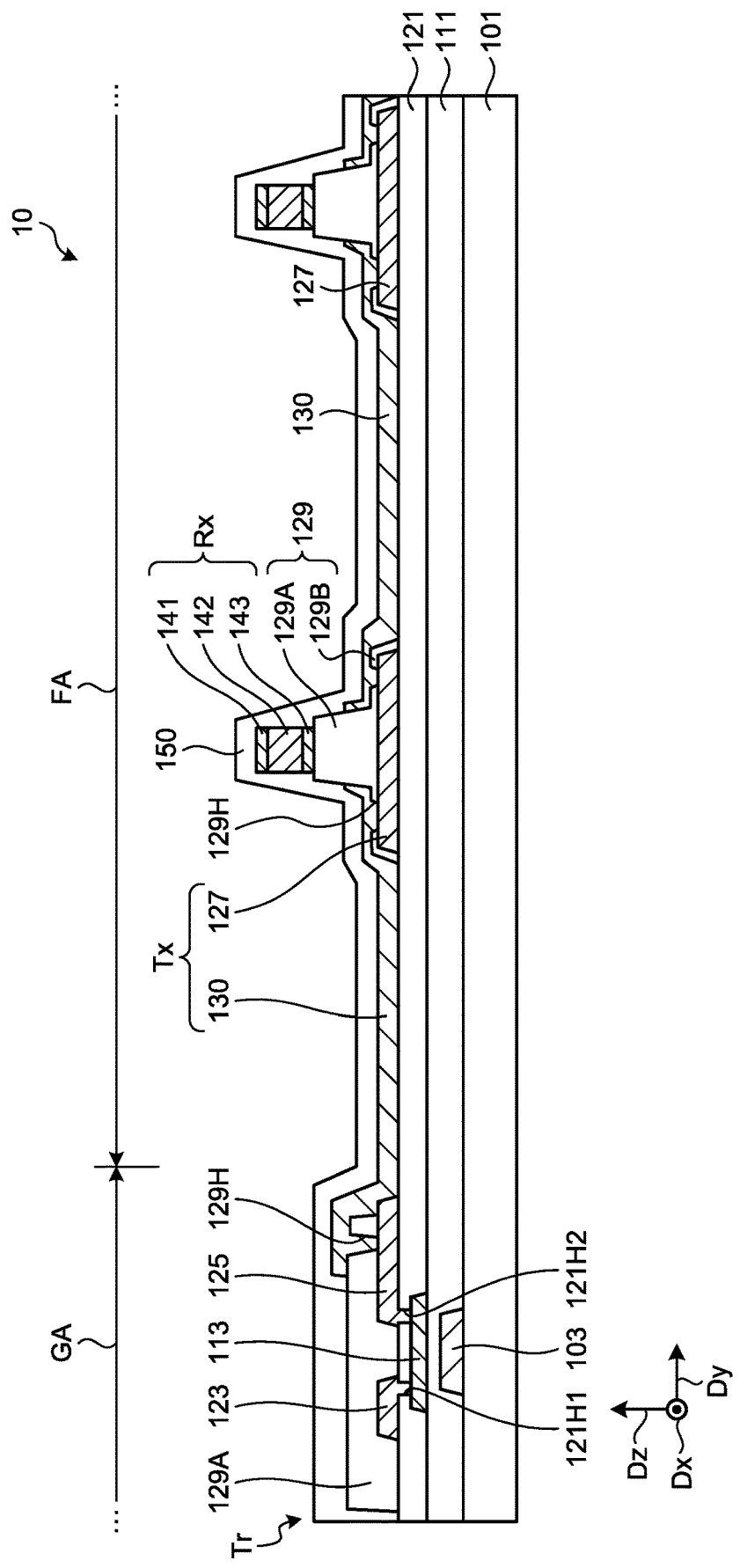
FIG. 14 is a sectional view illustrating a configuration example of the fingerprint sensor.

The following describes a layer structure of the fingerprint sensor. FIG. 14 is a sectional view illustrating a configuration example of the fingerprint sensor. In FIG. 14, the section of the fingerprint detection region FA is obtained by cutting the plan view illustrated in FIG. 10 along the A13-A14 line. In FIG. 14, the section of the frame region GA is obtained by cutting a part including a thin film transistor Tr of the drive electrode driver 15 (refer to FIG. 3). FIG. 14 illustrates the section along the A13-A14 line of the fingerprint detection region FA and the section of the part including the thin film transistor Tr of the frame region GA by schematically connecting these parts in order to show a relation between the layer structure of the fingerprint detection region FA and the layer structure of the frame region GA.

As illustrated in FIG. 14, the fingerprint sensor 10 has the substrate 101, a gate electrode 103 provided on the substrate 101, and a first inter-layer insulating film 111 provided on the substrate 101 to cover the gate electrode 103. The gate electrode 103 is provided in the frame region GA. Aluminum (Al), copper (Cu), silver (Ag), molybdenum (Mo), or an alloy of these materials is used as the material of the gate electrode 103. A silicon oxide film (SiO), a silicon nitride film (SiN), or a silicon oxide nitride film (SiON) is used as the material of the first inter-layer insulating film 111. The first inter-layer insulating film 111 may be a film with a multilayered structure. The first inter-layer insulating film may be a film with a multilayered structure in which a silicon nitride film is formed on a silicon oxide film, for example.

The fingerprint sensor 10 includes: a semiconductor layer 113 formed on the first inter-layer insulating film 111; and a second inter-layer insulating film 121 formed on the first inter-layer insulating film 111 to cover the semiconductor layer 113. The second inter-layer insulating film 121 is provided with contact holes 121H1 and 121H2. The semiconductor layer 113 is exposed at the bottom of the contact holes 121H1 and 121H2. A polysilicon or an oxide semiconductor is used as the material of the semiconductor layer 113. A silicon oxide film, a silicon nitride film, or a silicon oxide nitride film is used as the material of the second inter-layer insulating film 121. The second inter-layer insulating film 121 is not limited to a single layer and may be a film with a multilayered structure. The second inter-layer insulating film 121 may be a film with a multilayered structure in which a silicon nitride film is formed on a silicon oxide film, for example.

The fingerprint sensor 10 includes a source electrode 123, a drain electrode 125, and the connecting portions 127 provided on the second inter-layer insulating film 121. The source electrode 123 is embedded in the contact hole 121H1. The drain electrode 125 is embedded in the contact hole 121H2. With this structure, the source electrode 123 is connected to the semiconductor layer 113 via the contact hole 121H1. The drain electrode 125 is connected to the semiconductor layer 113 via the contact hole 121H2. Titanium aluminum (TiAl), which is an alloy of titanium and aluminum, is used as the materials of the source electrode 123, the drain electrode 125, and the connecting portions 127.

The gate electrode 103, the semiconductor layer 113, the source electrode 123, and the drain electrode 125 described above are provided in the frame region GA. The gate electrode 103, the semiconductor layer 113, the source electrode 123, and the drain electrode 125 constitute the thin film transistor Tr in the frame region GA.

The insulating film 129 is provided on the second inter-layer insulating film 121. As described above, the insulating film 129 includes the first insulating film 129A and the second insulating film 129B thinner than the first insulating film 129A. The first insulating film 129A provided in the frame region GA covers the source electrode 123 and the drain electrode 125. The first insulating film 129A provided in the frame region GA is provided with the contact hole 129H. The first insulating film 129A provided in the fingerprint detection region FA covers part of the connecting portion 127 positioned under the detection electrode Rx. The second insulating film 129B provided in the fingerprint detection region FA covers part of the connecting portion 127 positioned under the electrode portion 130. As described above, the second insulating film 129B is provided with the contact hole 129H.

Further, the electrode portions 130 are provided on the second inter-layer insulating film 121. In the fingerprint detection region FA, the peripheral parts of the electrode portions 130 (e.g., the protruding portions 132 illustrated in FIG. 13) are embedded in the contact hole 129H. With this structure, the electrode portions 130 are connected to the connecting portions 127 via the contact hole 129H. In this example, the electrode portions 130 are in contact with the second inter-layer insulating film 121.

In the fingerprint detection region FA, the detection electrodes Rx are provided on the first insulating film 129A. The first insulating film 129A insulates the detection electrodes Rx and the drive electrodes Tx from each other. The detection electrode Rx includes a first metallic layer 141, a second metallic layer 142, and a third metallic layer 143, for example. The second metallic layer 142 is provided on the third metallic layer 143, and the first metallic layer 141 is provided on the second metallic layer 142. Molybdenum or a molybdenum alloy is used as the materials of the first metallic layer 141 and the third metallic layer 143, for example. Aluminum or an aluminum alloy is used as the material of the second metallic layer 142. Molybdenum or a molybdenum alloy forming the first metallic layer 141 has a reflectance of visible light lower than that of aluminum or an aluminum alloy forming the second metallic layer 142.

The insulating film 150 is provided above the insulating film 129, the electrode portions 130, and the detection electrodes Rx. The insulating film 150 covers upper surfaces and side surfaces of the detection electrodes Rx. A film with a high refractive index and a low reflectance such as a silicon nitride film is used as the insulating film 150. Alternatively, the insulating film 150 may be a light-shielding resin film (e.g., a black resin film).

As described above, the fingerprint sensor 10 according to the first embodiment includes the drive electrodes Tx and the detection electrodes Rx both provided on the one surface 101*a* side of the substrate 101. The drive electrodes Tx are arranged in the first direction Dx. The detection electrodes Rx are arranged in the second direction Dy orthogonal to the first direction Dx. When viewed in the normal direction Dz, the shape of the detection electrodes Rx is a zigzag line. The detection electrodes Rx zigzag in the first direction Dx. Specifically, the detection electrodes Rx have a plurality of first line portions RxL1, a plurality of second line portions RxL2, and a plurality of bent portions RxB. The second line portions RxL2 extend in a direction intersecting the first line portions RxL1. The bent portions RxB connect the first line portions RxL1 and the second line portions RxL2 to each other. With this structure, the fingerprint sensor 10 can reduce the occurrence of unintended patterns such as moire, in comparison with a case in which the shape of the detection electrodes Rx when viewed from the normal direction Dz is a straight line.

The drive electrodes Tx have a plurality of electrode portions 130 arranged spaced apart from each other and the connecting portions 127 connecting adjacent electrode portions among the electrode portions 130 to each other. When viewed from the normal direction Dz of the substrate 101, one detection electrode Rx passes through a gap between adjacent electrode portions 130 and intersects the connecting portions 127. With this structure, the electrode portions 130 of the drive electrodes Tx can be arranged along the detection electrodes Rx.

The electrode portions 130 include the first electrode portion 130A and the second electrode portion 130B different in shape from the first electrode portion 130A when viewed from the normal direction Dz. With this structure, the first electrode portions 130A can be arranged along the first line portions RxL1, whereas the second electrode portions 130B can be arranged along the second line portions RxL2. In addition, the separating distance d3 between the electrode main body 131 and the detection electrode Rx can be a constant length. With this structure, the fingerprint sensor 10 can reduce variations in capacitance of the detection electrodes Rx due to the separating distance d3.

The fingerprint sensor 10 further includes the first insulating film 129A arranged between the connecting portion 127 and the detection electrode Rx and the second insulating film 129B arranged between the connecting portion 127 and the electrode portion 130. The second insulating film 129B is thinner than the first insulating film 129A. This structure allows the fingerprint sensor 10 to reduce a level difference of the electrode portion 130 in comparison with a case in which the electrode portion 130 is arranged on the first insulating film 129A. This structure can lower the probability of disconnection in the electrode portion 130. The first insulating film 129A arranged between the connecting portion 127 and the detection electrode Rx is larger in thickness than the second insulating film 129B, and thus can reduce capacitance of the detection electrodes Rx.

The electrode portions 130 are translucent electrodes, whereas the detection electrodes Rx are metallic thin lines. This structure can reduce resistance and capacitance of the detection electrodes Rx. The detection electrodes Rx are metallic thin lines and are thus small in electrode width. This structure can reduce the area covered with the detection electrodes Rx. Consequently, the fingerprint sensor 10 can increase the aperture of the fingerprint detection region FA and increase the translucency of the fingerprint detection region FA.

In the first direction Dx, the ratio of the arrangement pitch Prx of the bent portions RxB to the arrangement pitch Pt of the drive electrodes Tx is preferably 2 or less. With this structure, the fingerprint sensor 10 can reduce the occurrence of unintended patterns such as moire.

Modifications

The above has described the first embodiment, in which the electrode portions 130 including the first electrode portion 130A and the second electrode portion 130B different in shape from the first electrode portion 130A as illustrated in FIG. 10. However, in the present embodiment, the configuration of the electrode portions 130 is not limited to this example.

Figure 15:
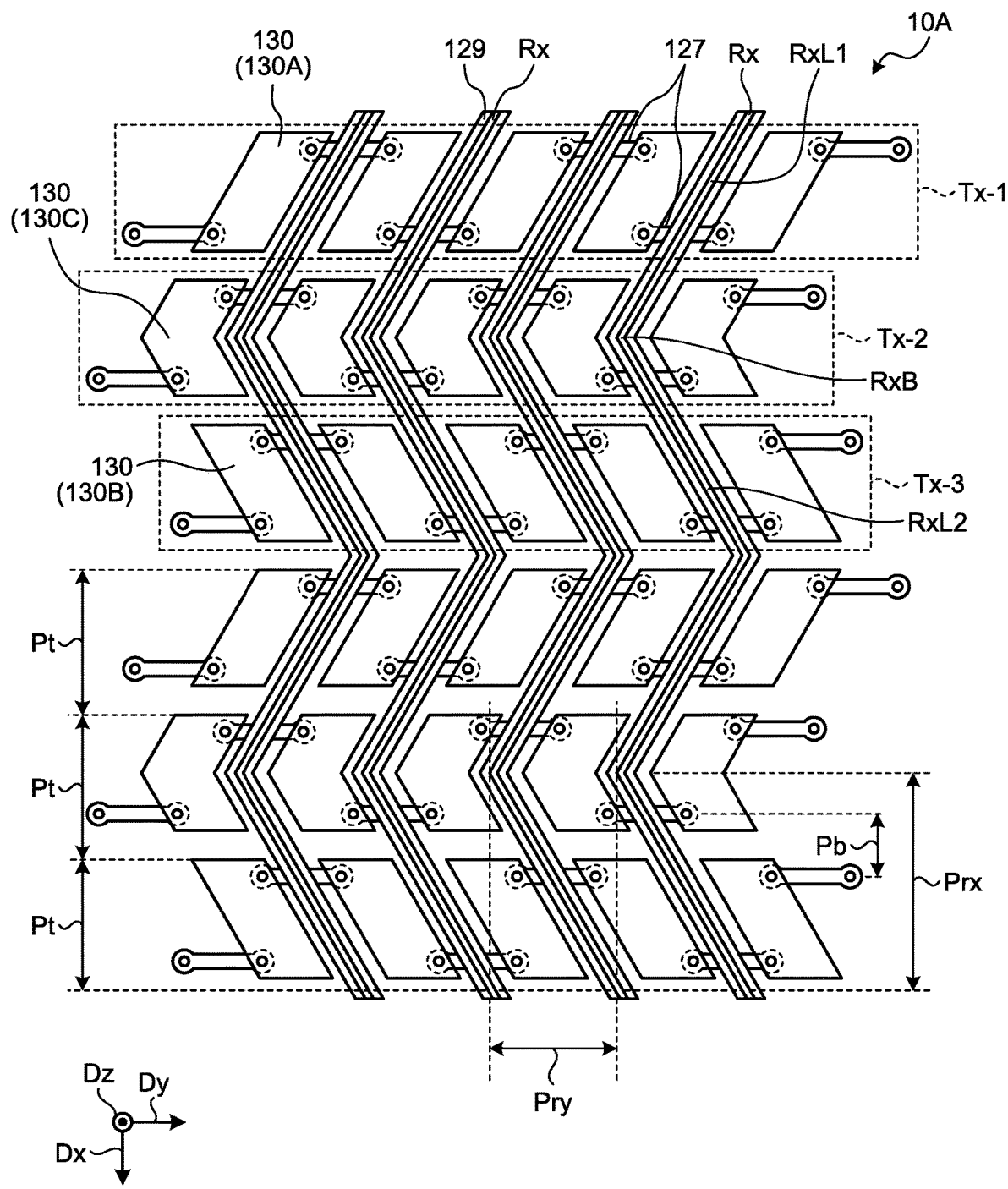
FIG. 15 is a plan view illustrating a fingerprint sensor according to a first modification of the first embodiment.

FIG. 15 is a plan view illustrating a fingerprint sensor according to a first modification of the first embodiment. As illustrated in FIG. 15, the electrode portions 130 may include the first electrode portion 130A, the second electrode portion 130B, and a third electrode portion 130C. The third electrode portion 130C is different from the first electrode portion 130A and the second electrode portion 130B in the shape of the electrode main body 131 (refer to FIG. 13).

As illustrated in FIG. 15, in a fingerprint sensor 10A according to the first modification, a drive electrode Tx-1 intersecting the first line portions RxL1 of the detection electrodes Rx includes the first electrode portions 130A each having two sides parallel to the first line portions RxL1. A drive electrode Tx-3 intersecting the second line portions RxL2 of the detection electrodes Rx includes the second electrode portions 130B each having two sides parallel to the second line portions RxL2. A drive electrode Tx-2 intersecting part of the detection electrodes Rx including the bent portions RxB includes the third electrode portions 130C. When viewed from the normal direction Dz, the shape of the third electrode portion 130C is a hexagon having two sides parallel to the first line portions RxL1 and two sides parallel to the second line portions RxL2. With this structure, also in the fingerprint sensor 10A according to the first modification, the electrode main bodies 131 of the electrode portions 130 can be arranged along the zigzag detection electrode Rx, and the separating distance d3 between the detection electrode Rx and the electrode main bodies 131 (refer to FIG. 13) can be a constant length.

The fingerprint sensor 10A also has the zigzag detection electrodes Rx. With this structure, the fingerprint sensor 10A can reduce the occurrence of unintended patterns such as moire.

Figure 16:
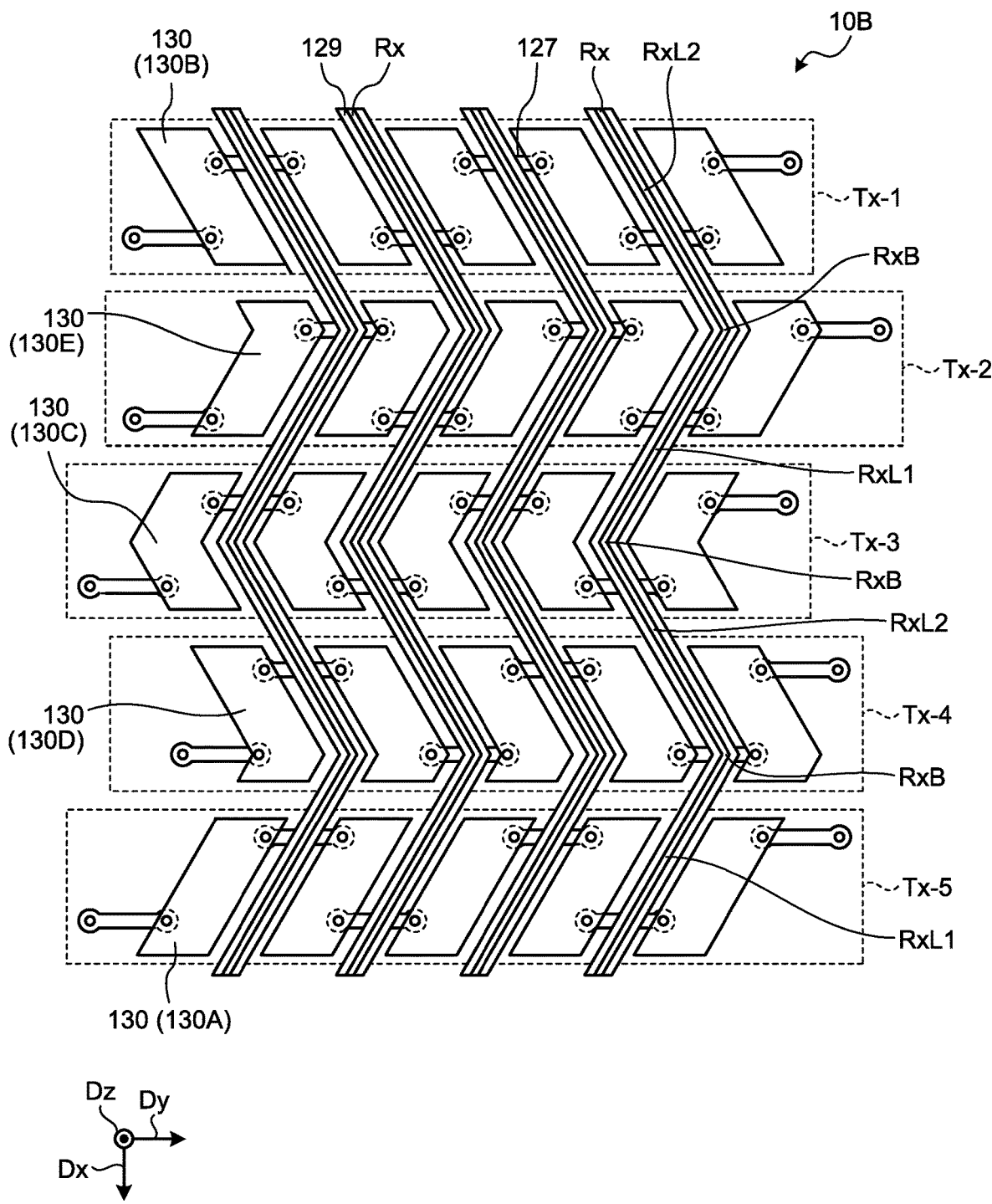
FIG. 16 is a plan view illustrating a fingerprint sensor according to a second modification of the first embodiment.

FIG. 16 is a plan view illustrating a fingerprint sensor according to a second modification of the first embodiment. As illustrated in FIG. 16, the electrode portions 130 may include the first electrode portion 130A, the second electrode portion 130B, the third electrode portion 130C, a fourth electrode portion 130D, and a fifth electrode portion 130E. The fourth electrode portion 130D and the fifth electrode portion 130E are different from the first electrode portion 130A, the second electrode portion 130B, and the third electrode portion 130C in the shape of the electrode main body 131 (refer to FIG. 13).

As illustrated in FIG. 16, in a fingerprint sensor 10B according to the second modification of the first embodiment, the drive electrode Tx-1 intersecting the second line portions RxL2 of the detection electrodes Rx includes the second electrode portions 130B each having two sides parallel to the second line portions RxL2. A drive electrode Tx-5 intersecting the first line portions RxL1 of the detection electrodes Rx includes the first electrode portions 130A each having two sides parallel to the first line portions RxL1. The drive electrodes Tx-2, Tx-3, and Tx-4 each intersect part of the detection electrodes Rx including the bent portions RxB. The drive electrode Tx-2 includes the fifth electrode portions 130E. The drive electrode Tx-3 includes the third electrode portions 130C. The drive electrode Tx-4 includes the fourth electrode portions 130D.

When viewed from the normal direction Dz, each of the shape of the third electrode portion 130C, the shape of the fourth electrode portion 130D, and the shape of the fifth electrode portion 130E is a hexagon having two sides parallel to the first line portions RxL1 and two sides parallel to the second line portions RxL2. When viewed from the normal direction Dz, the shape of the electrode main body 131 of the fifth electrode portion 130E is obtained by vertically flipping the shape of the electrode main body 131 of the fourth electrode portion 130D. With this structure, also in the fingerprint sensor 10B according to the second modification, the electrode main bodies 131 can be arranged along the zigzag detection electrode Rx, and the separating distance d3 between the detection electrode Rx and the electrode main bodies 131 (refer to FIG. 13) can be a constant length.

The fingerprint sensor 10B also has the zigzag detection electrodes Rx. With this structure, the fingerprint sensor 10B can reduce the occurrence of unintended patterns such as moire.

In the present embodiment, the shape of the second electrode portion 130B in a plan view is not limited to the shape described above. The shape of the second electrode portion 130B in a plan view may be a polygon other than a parallelogram. The same as the second electrode portion 130B can be applied to the third electrode portion 130C, the fourth electrode portion 130D, and the fifth electrode portion 130E. Each of the shape of the third electrode portion 130C, the shape of the fourth electrode portion 130D, and the shape of the fifth electrode portion 130E in a plan view may be a parallelogram different from the shape of the first electrode portion 130A, a hexagon other than the shape illustrated in FIG. 16, or a polygon other than the hexagon.

The above has described the first embodiment exemplified by the mode in which the slits (gaps) between the electrode portions 130 adjacent to each other in the first direction Dx are arranged linearly in the second direction Dy. However, in the present embodiment, the slits between the electrode portions 130 adjacent to each other in the first direction Dx are not necessarily arranged linearly in the second direction Dy.

Figure 17:
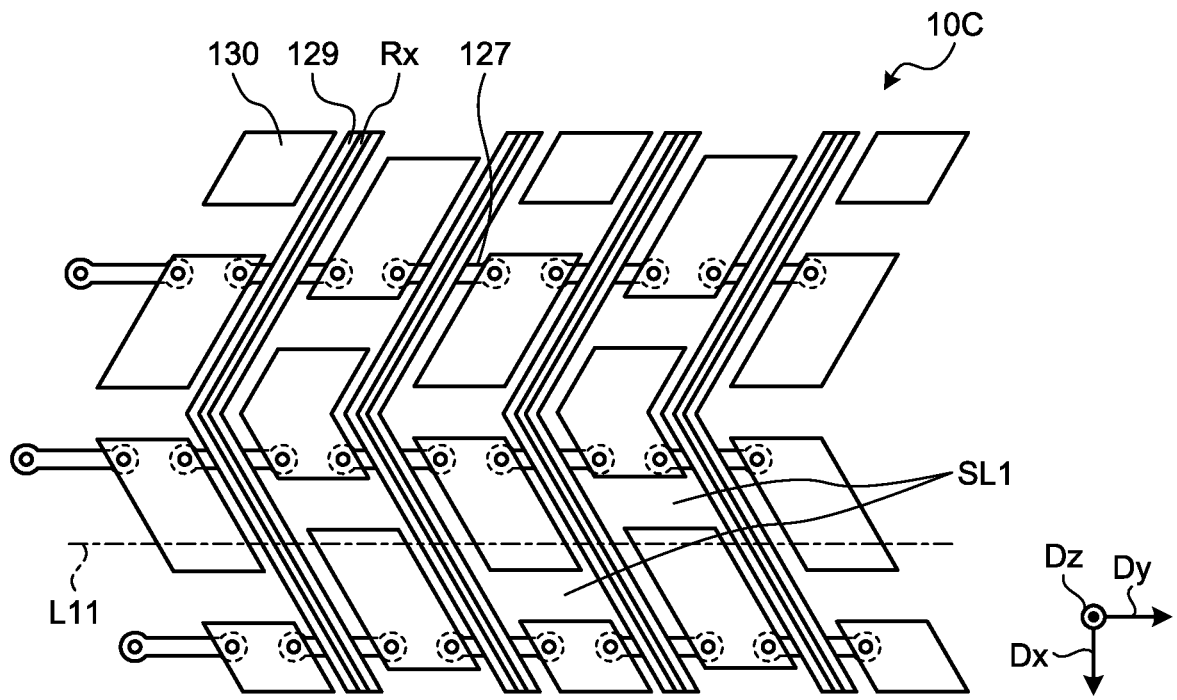
FIG. 17 is a plan view illustrating a fingerprint sensor according to a third modification of the first embodiment.

FIG. 17 is a plan view illustrating a fingerprint sensor according to a third modification of the first embodiment. As illustrated in FIG. 17, in a fingerprint sensor 10C according to the third modification of the first embodiment, for example, a plurality of slits SL1 arranged in the second direction Dy are arranged laterally alternately across a first virtual line L11 parallel to the second direction Dy.

The fingerprint sensor 10C also has the zigzag detection electrodes Rx. With this structure, the fingerprint sensor 10C can reduce the occurrence of unintended patterns such as moire. In the fingerprint sensor 10C, the slits SL1, light transmittance of which is different from that of the electrode portions 130, are not arranged linearly. With this structure, the fingerprint sensor 10C may be able to further reduce the occurrence of unintended patterns such as moire.

The fingerprint sensor according to the present embodiment may include a dummy electrode between the electrode portions 130 adjacent to each other in the first direction Dx. The dummy electrode refers to an electrode that is not connected to other conductive parts and is in a floating state, in which the potential is not fixed.

Figure 18:
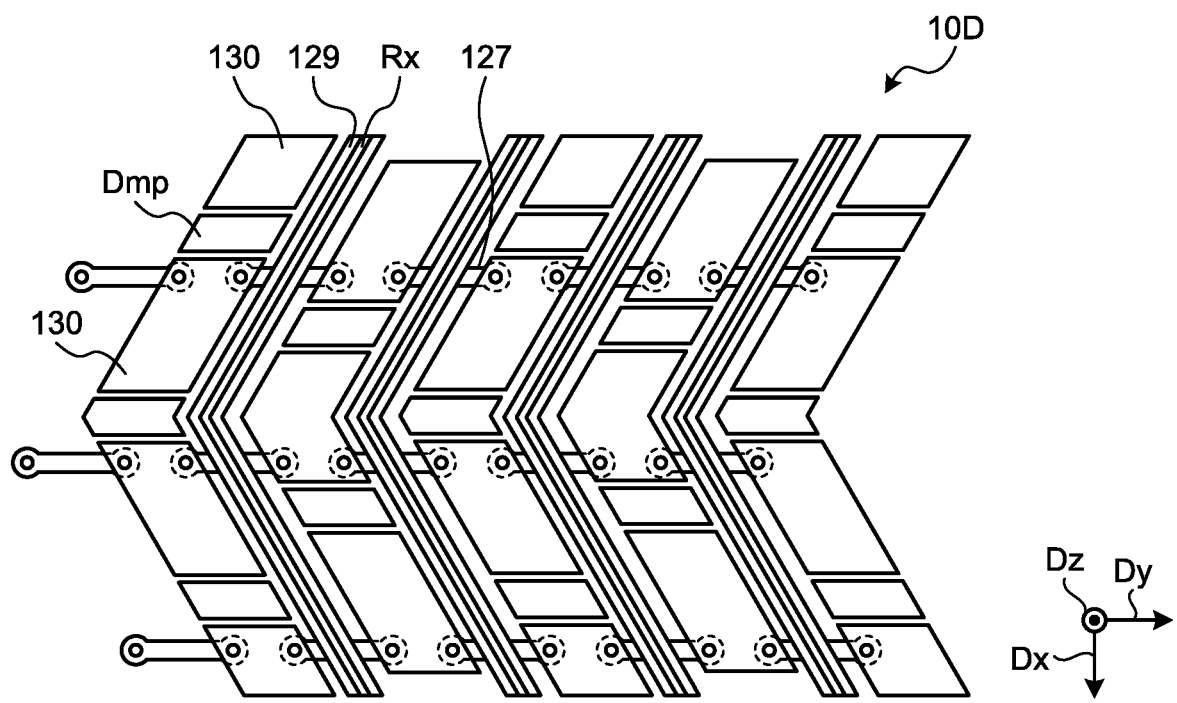
FIG. 18 is a plan view illustrating a fingerprint sensor according to a fourth modification of the first embodiment.

FIG. 18 is a plan view illustrating a fingerprint sensor according to a fourth modification of the first embodiment. As illustrated in FIG. 18, for example, a fingerprint sensor 10D according to the fourth modification of the first embodiment has a dummy electrode Dmp between the electrode portions 130 adjacent to each other in the first direction Dx. As described above, the dummy electrode Dmp is in the floating state, in which the potential is not fixed. The dummy electrode Dmp is formed simultaneously with the electrode portions 130 at the same process. With this process, the dummy electrode Dmp is formed of a conductive film with the same material and the same thickness as those of the electrode portions 130.

The fingerprint sensor 10D also has the zigzag detection electrodes Rx. With this structure, the fingerprint sensor 10D can reduce the occurrence of unintended patterns such as moire. In the fingerprint sensor 10D, the dummy electrode Dmp with the same material and the same thickness as those of the electrode portions 130 is arranged between the electrode portions 130 adjacent to each other in the first direction Dx. This structure reduces an optical difference between the electrode portions 130, whereby the fingerprint sensor 10D may be able to further reduce the occurrence of unintended patterns such as moire.

In the present embodiment, the electrode portions 130 may be provided with slits.

Figure 19:
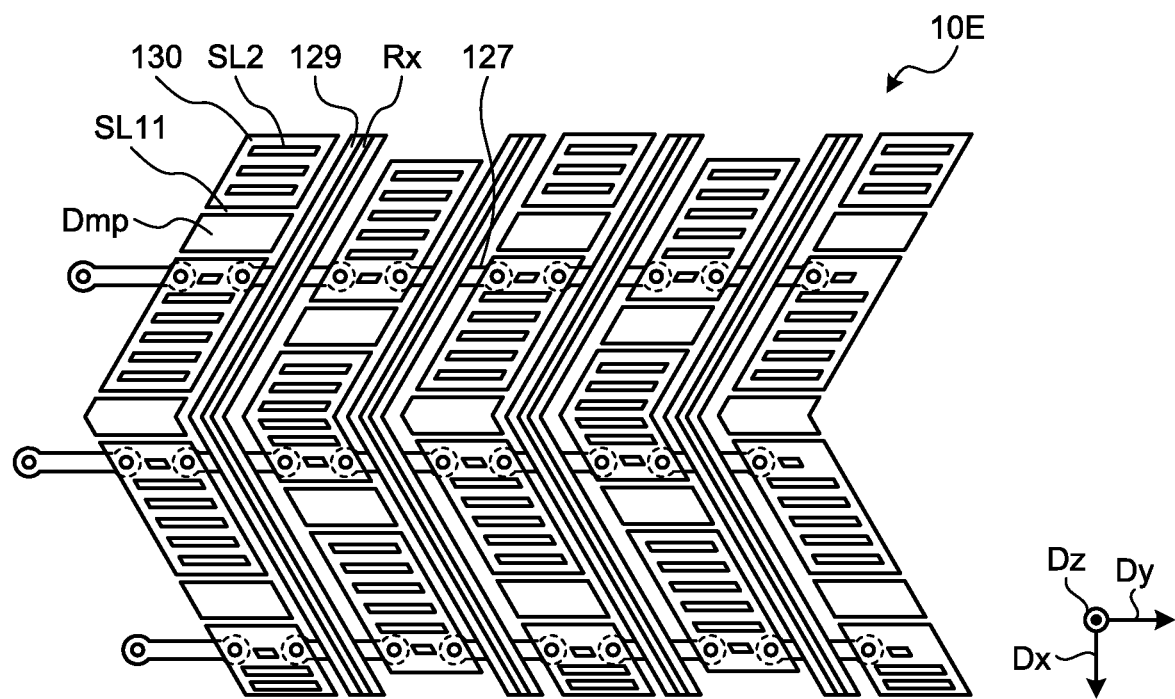
FIG. 19 is a plan view illustrating a fingerprint sensor according to a fifth modification of the first embodiment.

FIG. 19 is a plan view illustrating a fingerprint sensor according to a fifth modification of the first embodiment. As illustrated in FIG. 19, in a fingerprint sensor 10E according to the fifth modification of the first embodiment, the electrode portion 130 is provided with one or more slits SL2. The slit SL2 is a through hole having a long and narrow shape in a plan view and passing through the electrode portion 130. When each electrode portion 130 is provided with a plurality of slits SL2, the slits SL2 may be equally spaced or unequally spaced. As illustrated in FIG. 19, the slits SL2 provided in each electrode portion 130 and a slit (gap) SL11 provided between the electrode portion 130 and the dummy electrode Dmp may be equally spaced or substantially equally spaced.

The fingerprint sensor 10E also has the zigzag detection electrodes Rx. With this structure, the fingerprint sensor 10E can further reduce the occurrence of unintended patterns such as moire. The fingerprint sensor 10E may be able to further reduce the occurrence of unintended patterns such as moire by having the slits SL2 and SL11.

Figure 20:
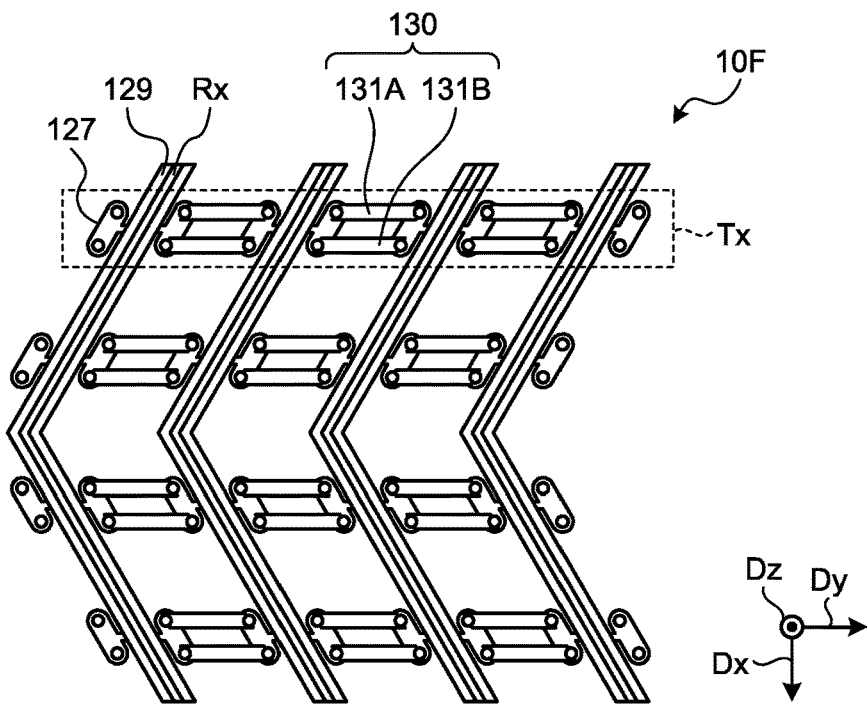
FIG. 20 is a plan view illustrating a fingerprint sensor according to a sixth modification of the first embodiment.

FIG. 20 is a plan view illustrating a fingerprint sensor according to a sixth modification of the first embodiment. As illustrated in FIG. 20, in a fingerprint sensor 10F according to the sixth modification of the first embodiment, the electrode portions 130 of the drive electrodes Tx include wire-shaped electrode main bodies 131A and 131B. A conductive material having translucency such as ITO, for example, is used for the electrode main bodies 131A and 131B. One end of each of the electrode main bodies 131A and 131B is connected to one connecting portion 127, and the other end of each of the electrode main bodies 131A and 131B is connected to another connecting portion 127 adjacent to the one connecting portion 127.

The fingerprint sensor 10F also has the zigzag detection electrodes Rx. With this structure, the fingerprint sensor 10F can reduce the occurrence of unintended patterns such as moire. This structure reduces the area of the electrode portions 130, thereby allowing the fingerprint sensor 10F to reduce the capacitance of the detection electrodes Rx.

Second Embodiment

The above has described the first embodiment in which the connecting portion 127 is connected to the electrode portion 130 via the contact hole 129H. However, in the present embodiment, the connecting portion 127 may be connected to the electrode portion 130 without via a contact hole. The electrode portions 130 adjacent to each other in the second direction Dy may be connected to each other via a conductive film formed simultaneously with the electrode portions 130 at the same process.

Figure 21:
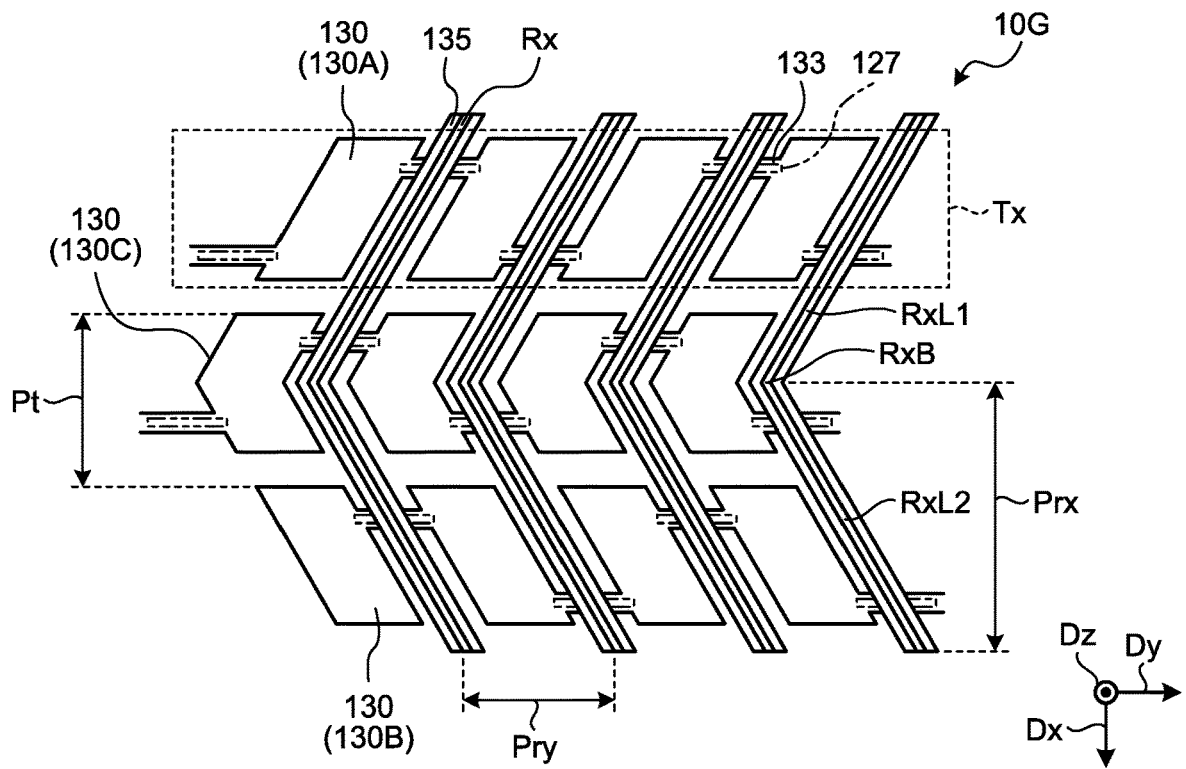
FIG. 21 is a plan view illustrating a configuration example of a fingerprint sensor according to a second embodiment.
Figure 22:
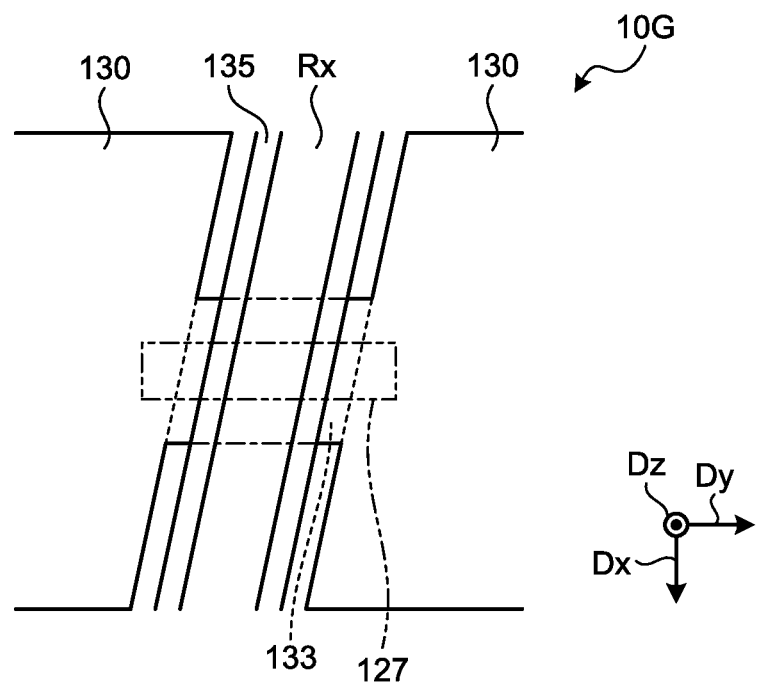
FIG. 22 is a plan view illustrating a drive electrode and a detection electrode according to the second embodiment.
Figure 23:
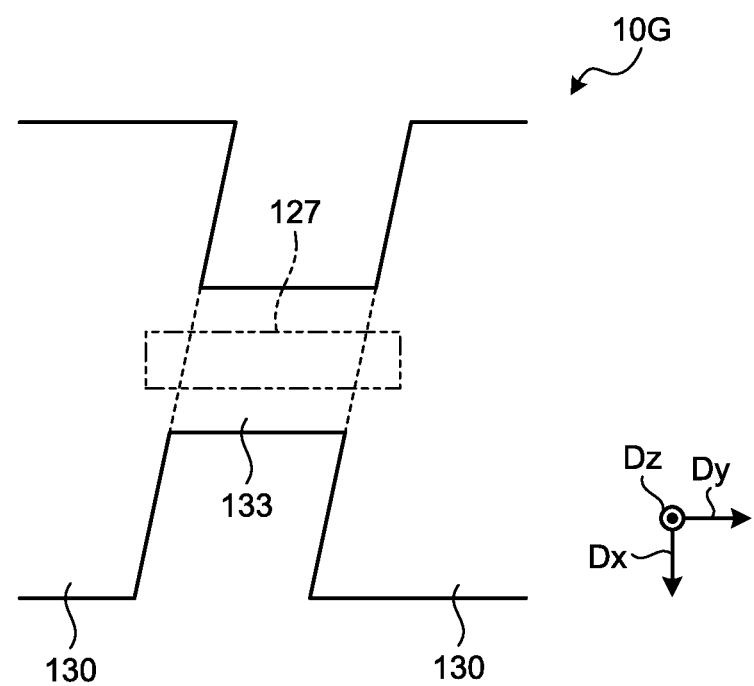
FIG. 23 is a diagram omitting the illustration of the detection electrode and an insulating film in FIG. 22.

FIG. 21 is a plan view illustrating a configuration example of a fingerprint sensor according to a second embodiment. FIG. 22 is a plan view illustrating the drive electrode and the detection electrode. FIG. 23 is a diagram omitting the illustration of the detection electrode and an insulating film in FIG. 22. As illustrated in FIG. 21, in a fingerprint sensor 10G according to the second embodiment, one drive electrode Tx has a plurality of electrode portions 130, a plurality of connecting portions (hereinafter, first connecting portions) 127, and a plurality of second connecting portions 133. In one drive electrode Tx, the electrode portions 130 are arranged in the second direction Dy and are spaced apart from each other. In one drive electrode Tx, the first connecting portion 127 and the second connecting portion 133 each connect adjacent electrode portions among the electrode portions 130 to each other. For example, the second connecting portion 133 is provided on the first connecting portion 127.

As illustrated in FIG. 22 and FIG. 23, one end of the first connecting portion 127 is in contact with a surface of one electrode portion 130 and the other end of the first connecting portion 127 is in contact with a surface of another electrode portion 130 adjacent to the one electrode portion 130, the surfaces facing the substrate 101. The second connecting portion 133 is a film formed simultaneously with the electrode portions 130 at the same process. The second connecting portion 133 is integral with the electrode portions 130. An insulating film 135 is provided between the second connecting portion 133 and the detection electrode Rx. With this structure, the detection electrodes Rx and the drive electrodes Tx are insulated from each other. The insulating film 135 is a resin insulating film, for example.

With this configuration, the fingerprint sensor 10G also can reduce the occurrence of unintended patterns such as moire. Further, the configuration can reduce the size of the connecting portions 127, and reduce the area occupied by the connecting portions 127. With this structure, the fingerprint sensor 10G can further increase aperture of the fingerprint detection region FA and further increase the translucency of the fingerprint detection region FA.

Figure 24:
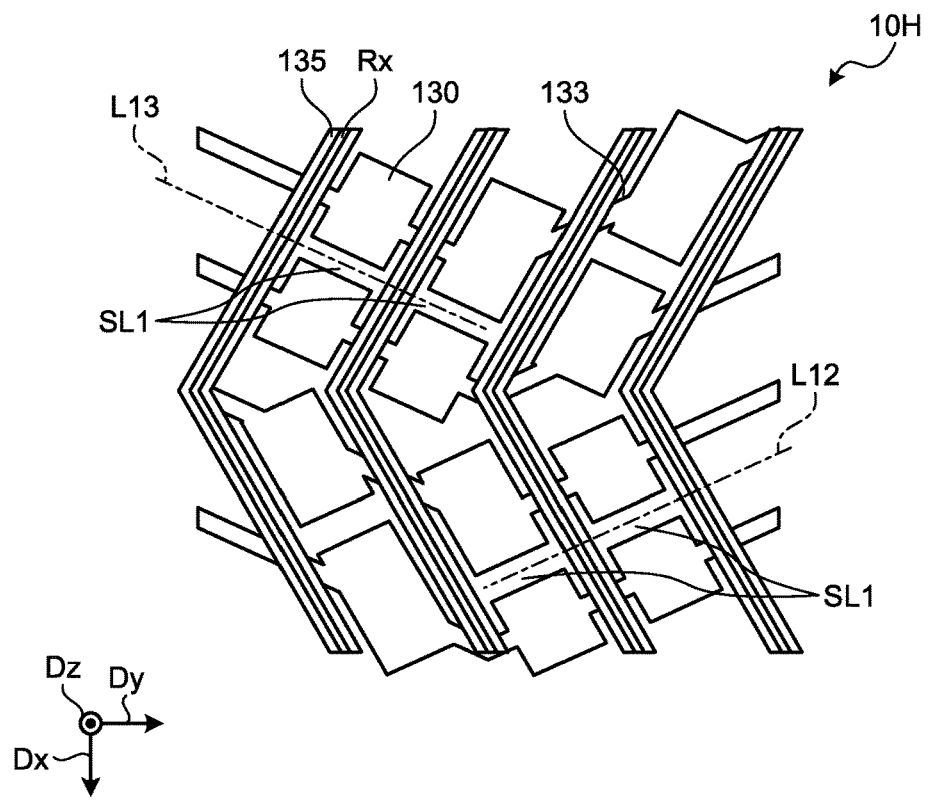
FIG. 24 is a plan view illustrating a fingerprint sensor according to a first modification of the second embodiment.

FIG. 24 is a plan view illustrating a fingerprint sensor according to a first modification of the second embodiment. As illustrated in FIG. 24, in a fingerprint sensor 10H according to the first modification of the second embodiment, a plurality of slits SL1 arranged in the second direction Dy zigzag in the second direction Dy. The electrode portions 130 arranged in the second direction Dy are in alternately parallel to a second virtual line L12 and a third virtual line L13, for example. The slits SL1 arranged in the second direction Dy are also in alternately parallel to the second virtual line L12 and the third virtual line L13. In a plan view, the second virtual line L12 is a straight line in a direction intersecting the first direction and the second direction, whereas the third virtual line L13 is a straight line in a direction intersecting the second virtual line L12.

The fingerprint sensor 10H also has the zigzag detection electrodes Rx. With this structure, the fingerprint sensor 10H can reduce the occurrence of unintended patterns such as moire. The slits SL1 are arranged zigzag in the second direction Dy. With this structure, the fingerprint sensor 10H may be able to further reduce the occurrence of unintended patterns such as moire.

Figure 25:
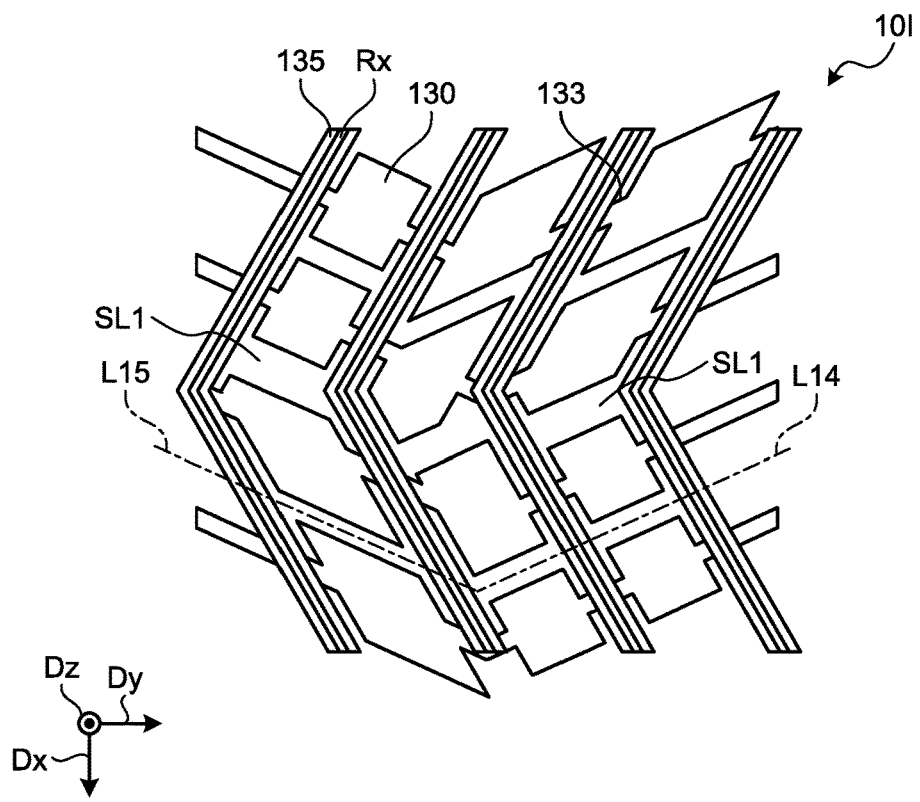
FIG. 25 is a plan view illustrating a fingerprint sensor according to a second modification of the second embodiment.

FIG. 25 is a plan view illustrating a fingerprint sensor according to a second modification of the second embodiment. As illustrated in FIG. 25, a fingerprint sensor 10I according to the second modification of the second embodiment includes the electrode portion 130, the shape in a plan view of which is a parallelogram and the electrode portion 130 the shape in a plan view of which is a pentagon. The electrode portions 130 arranged in the second direction Dy are in alternately parallel to a fourth virtual line L14 and a fifth virtual line L15. The slits SL1 arranged in the second direction Dy are also in alternately parallel to the fourth virtual line L14 and the fifth virtual line L15. In a plan view, the fourth virtual line L14 is a straight line in a direction intersecting the first direction and the second direction, whereas the fifth virtual line L15 is a straight line in a direction intersecting the fourth virtual line L14.

The fingerprint sensor 10I also has the zigzag detection electrodes Rx. With this structure, the fingerprint sensor 10I can reduce the occurrence of unintended patterns such as moire. The slits SL1 are arranged zigzag in the second direction Dy. With this structure, the fingerprint sensor 10I may be able to further reduce the occurrence of unintended patterns such as moire.

Third Embodiment

Figure 26:
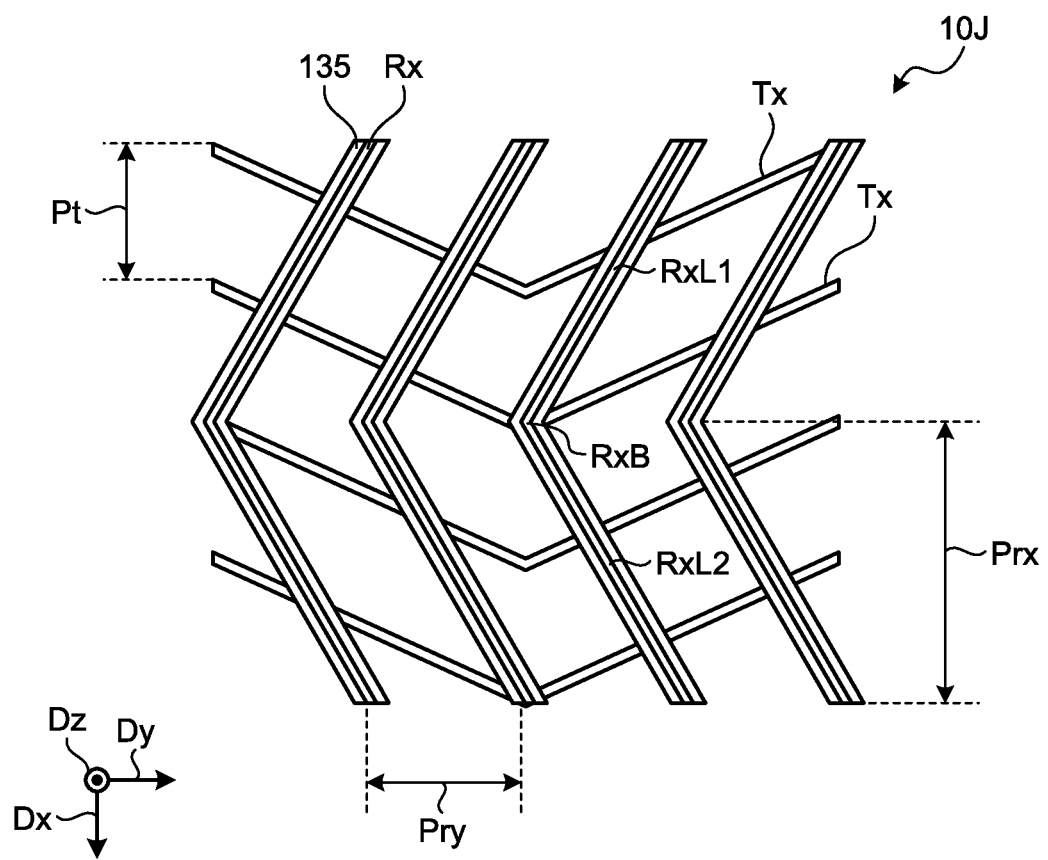
FIG. 26 is a plan view illustrating a configuration example of a fingerprint sensor according to a third embodiment.

FIG. 26 is a plan view illustrating a configuration example of a fingerprint sensor according to a third embodiment. As illustrated in FIG. 26, in a fingerprint sensor 10J according to the third embodiment, each of the drive electrodes Tx is formed of one metallic thin line. Aluminum, copper, silver, molybdenum, or an alloy of these is used for the material of the metallic thin line forming the drive electrodes Tx. The insulating film 135 is provided between the drive electrodes Tx and the detection electrodes Rx. With this structure, the detection electrodes Rx and the drive electrodes Tx are insulated from each other.

With this configuration, the fingerprint sensor 10J can reduce the resistance of the drive electrodes Tx. Further, the fingerprint sensor 10J can reduce the capacitance of the drive electrodes Tx.

Fourth Embodiment

Figure 27:
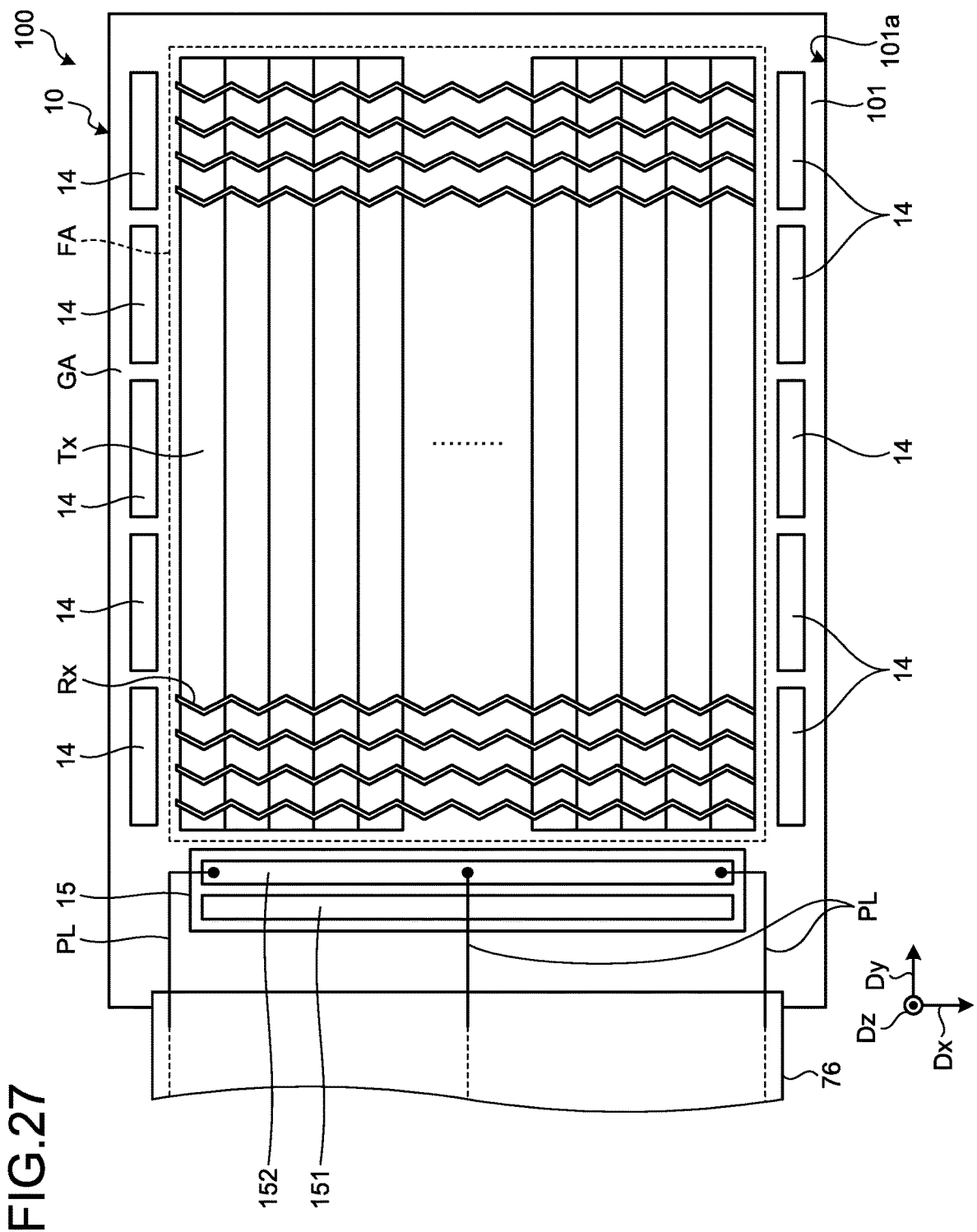
FIG. 27 is a block diagram illustrating a configuration example of a fingerprint detection device according to a fourth embodiment.
Figure 28:
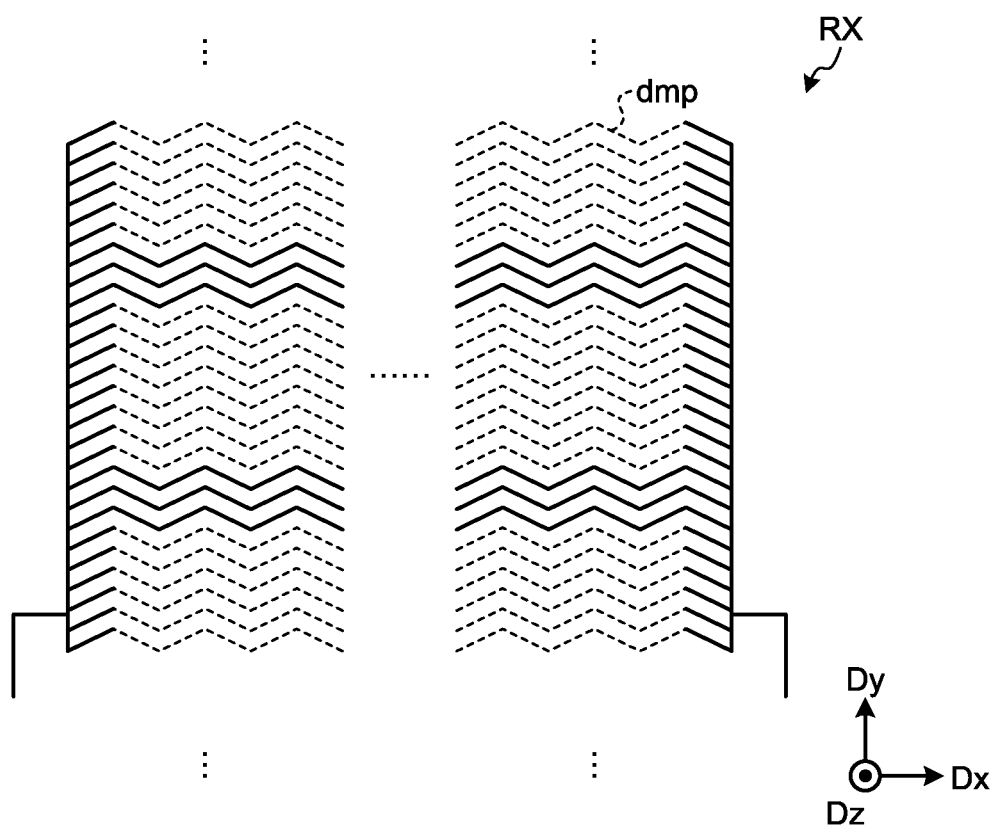
FIG. 28 is a plan view illustrating a configuration example of the detection electrodes according to the fourth embodiment.
Figure 29:
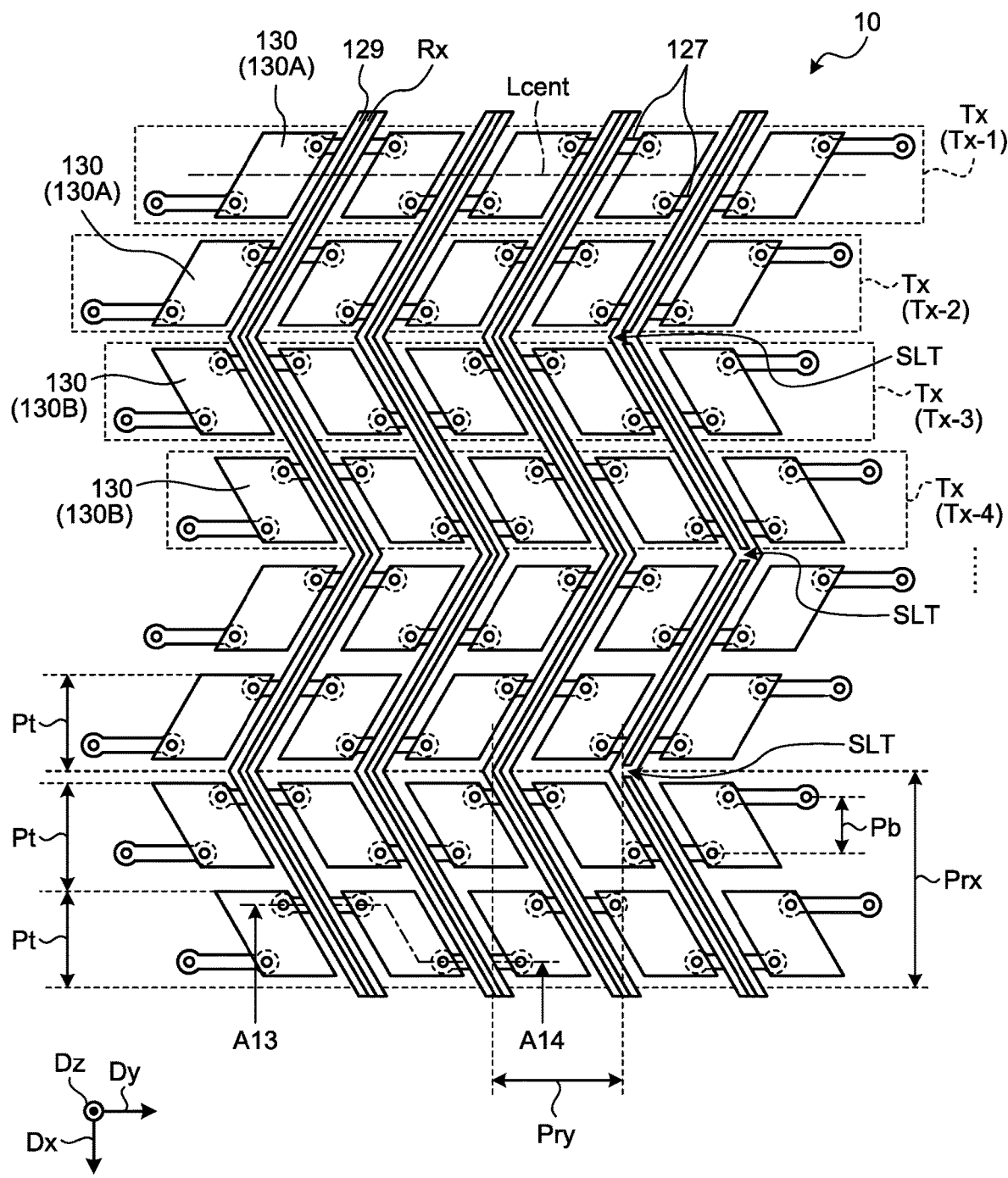
FIG. 29 is a plan view illustrating a configuration example of the detection electrodes according to the fourth embodiment.

FIG. 27 is a block diagram illustrating a configuration example of the fingerprint detection device according to a fourth embodiment. FIG. 28 is a plan view illustrating a configuration example of the detection electrodes according to the fourth embodiment. FIG. 29 is a plan view illustrating a configuration example of the detection electrodes according to the fourth embodiment. FIG. 29 is a partially enlarged view illustrating FIG. 28. In the fourth embodiment, the drive electrode driver 15 and the drive electrodes Tx are arranged in the second direction Dy in which the drive electrodes Tx extend. The detection electrode selection circuits 14 are arranged in the first direction Dx so as to hold the drive electrodes Tx therebetween.

The drive electrode driver 15 includes a shift register circuit 151 and a buffer circuit 152. The shift register circuit 151 sequentially selects the drive electrodes Tx in a time division manner. The buffer circuit 152 amplifies the drive signal Vs and supplies it to a selected drive electrode Tx. A plurality of power supply lines PL supply power to the buffer circuit 152 from the outside. The power supply lines PL supply power to both ends of the buffer circuit 152 and the central part thereof in the second direction Dy, for example. With this operation, without supplying power from the upper side, power can be directly supplied to the buffer circuit 152 from the outside of the drive electrode driver 15, and a load during power supply is reduced.

As illustrated in FIG. 28, dummy electrodes dmp are arranged such that conductive materials such as metal discontinue and are not continuous in the first direction. As illustrated in FIG. 29, slits SLT separate the conductive materials. This structure makes the detection electrodes Rx less noticeable and invisible.

While exemplary embodiments have been described, the embodiments are not intended to limit the present disclosure. The contents disclosed in the embodiments are given by way of example only, and various modifications may be made without departing from the spirit of the present disclosure. Although a transmissive liquid crystal display device capable of color display has been described as the display device 1 in the first embodiment, for example, the present disclosure is not limited to a transmissive liquid crystal display device supporting color display and may be a transmissive liquid crystal display device for monochrome display. Appropriate modifications made without departing from the gist of the present disclosure also naturally belong to the technical scope of the present disclosure.

The fingerprint detection device and the display device of the preset disclosure include the following aspects:

(1) A fingerprint detection device, comprising:
   a substrate;
   a plurality of drive electrodes provided on one surface side of the substrate and arranged in a first direction; and
   a plurality of detection electrodes provided on the one surface side and arranged in a second direction intersecting the first direction, wherein
   the detection electrodes intersect the drive electrodes in a normal direction of the substrate, and
   each of the detection electrodes includes:
      a plurality of first line portions;
      a plurality of second line portions extending in a direction intersecting the first line portions; and
      a plurality of bent portions each connecting one of the first line portions and one of the second line portions adjacent to the one of the first line portions to each other.

(2) A fingerprint detection device, comprising:
   a substrate;
   a plurality of drive electrodes provided on one surface side of the substrate and arranged in a first direction; and
   a plurality of detection electrodes provided on the one surface side and arranged in a second direction intersecting the first direction, wherein
   each of the drive electrodes includes:
      a plurality of electrode portions arranged spaced apart from each other in a plan view; and
      a plurality of connecting portions each connecting adjacent electrode portions of the electrode portions to each other,
   each of the electrode portions has a shape including two sides parallel to the drive electrodes, and
   each of the detection electrodes passes through a gap between the adjacent electrode portions and intersects the connecting portions in a plan view.

(3) The fingerprint detection device according to (1), wherein
   each of the drive electrodes includes:
      a plurality of electrode portions arranged spaced apart from each other in a plan view; and
      a plurality of connecting portions each connecting adjacent electrode portions of the electrode portions to each other, and
   each of the detection electrodes passes through a gap between the adjacent electrode portions and intersects the connecting portions in a plan view.

(4) The fingerprint detection device according to (2) or (3), wherein each of the electrode portions includes:
   a first electrode portion; and
   a second electrode portion different in shape from the first electrode in a plan view.

(5) The fingerprint detection device according to (4), wherein a shape of the first electrode portion in a plan view is a parallelogram having two sides parallel to the drive electrodes, and
a shape of the second electrode portion in a plan view is a parallelogram or a polygon having two sides parallel to the drive electrodes and different in shape from the first electrode portion.
(6) The fingerprint detection device according to any one of (3) to (5), further comprising:
a first insulating film arranged between the connecting portions and the corresponding detection electrodes in the normal direction of the substrate; and
a second insulating film arranged between the connecting portions and the corresponding electrode portions, wherein
the second insulating film is thinner than the first insulating film.
(7) The fingerprint detection device according to any one of (2) to (6), wherein
the electrode portions are translucent electrodes, and the detection electrodes are metallic thin lines.
(8) The fingerprint detection device according to (1), wherein a ratio of an arrangement pitch of the bent portions to an arrangement pitch of the drive electrodes is 2 or less in the first direction.
(9) The fingerprint detection device according to any one of (2) to (6), wherein the connecting portions are arranged alternately on one side and the other side relative to a virtual line passing through the center of gravity of the electrode portions in the second direction.
(10) A display device, comprising:
a display panel; and
a fingerprint detection device arranged facing the display panel, the fingerprint detection device comprising:
a substrate;
a plurality of drive electrodes provided on one surface side of the substrate and arranged in a first direction; and
a plurality of detection electrodes provided on the one surface side and arranged in a second direction intersecting the first direction, wherein
the detection electrodes intersect the drive electrodes in a normal direction of the substrate, and
each of the detection electrodes includes:
a plurality of first line portions;
a plurality of second line portions extending in a direction intersecting the first line portions; and
a plurality of bent portions each connecting one of the first line portions and one of the second line portions adjacent to the one of the first line portions to each other.

What is claimed is:
1. A fingerprint detection device, comprising:
a substrate;
a plurality of drive electrodes provided on one surface side of the substrate and arranged in a first direction; and
a plurality of detection electrodes provided on the one surface side and arranged in a second direction intersecting the first direction, wherein
the detection electrodes intersect the drive electrodes in a normal direction of the substrate, and
each of the detection electrodes includes:
a plurality of first line portions;
a plurality of second line portions extending in a direction intersecting the first line portions; and
a plurality of bent portions each connecting one of the first line portions and one of the second line portions adjacent to the one of the first line portions to each other,
each of the drive electrodes includes:
a plurality of electrode portions arranged spaced apart from each other in a plan view; and
a plurality of connecting portions each connecting adjacent electrode portions of the electrode portions to each other, and
each of the detection electrodes passes through a gap between the adjacent electrode portions and intersects the connecting portions in a plan view.
2. The fingerprint detection device according to claim 1, wherein each of the electrode portions includes:
a first electrode portion; and
a second electrode portion different in shape from the first electrode in a plan view.
3. The fingerprint detection device according to claim 2, wherein
a shape of the first electrode portion in a plan view is a parallelogram having two sides parallel to the drive electrodes, and
a shape of the second electrode portion in a plan view is a parallelogram or a polygon having two sides parallel to the drive electrodes and different in shape from the first electrode portion.
4. The fingerprint detection device according to claim 1, further comprising:
a first insulating film arranged between the connecting portions and the corresponding detection electrodes in the normal direction of the substrate; and
a second insulating film arranged between the connecting portions and the corresponding electrode portions, wherein
the second insulating film is thinner than the first insulating film.
5. The fingerprint detection device according to claim 1, wherein
the electrode portions are translucent electrodes, and the detection electrodes are metallic thin lines.
6. A fingerprint detection device, comprising:
a substrate;
a plurality of drive electrodes provided on one surface side of the substrate and arranged in a first direction; and
a plurality of detection electrodes provided on the one surface side and arranged in a second direction intersecting the first direction,
wherein
the detection electrodes intersect the drive electrodes in a normal direction of the substrate,
each of the detection electrodes includes: a plurality of first line portions;
a plurality of second line portions extending in a direction intersecting the first line portions; and
a plurality of bent portions each connecting one of the first line portions and one of the second line portions adjacent to the one of the first line portions to each other, and
a ratio of an arrangement pitch of the bent portions to an arrangement pitch of the drive electrodes is 2 or less in the first direction.
7. A fingerprint detection device, comprising:
a substrate;

a plurality of drive electrodes provided on one surface side of the substrate and arranged in a first direction; and a plurality of detection electrodes provided on the one surface side and arranged in a second direction intersecting the first direction, wherein each of the drive electrodes includes:
- a plurality of electrode portions arranged spaced apart from each other in a plan view; and
- a plurality of connecting portions each connecting adjacent electrode portions of the electrode portions to each other, each of the electrode portions has a shape including two sides parallel to the drive electrodes, and each of the detection electrodes passes through a gap between the adjacent electrode portions and intersects the connecting portions in a plan view.

8. The fingerprint detection device according to claim 7, wherein each of the electrode portions includes:
- a first electrode portion; and
- a second electrode portion different in shape from the first electrode portion in a plan view.

9. The fingerprint detection device according to claim 8, wherein
- a shape of the first electrode portion in a plan view is a parallelogram having two sides parallel to the drive electrodes, and
- a shape of the second electrode portion in a plan view is a parallelogram or a polygon having two sides parallel to the drive electrodes and different in shape from the first electrode portion.

10. The fingerprint detection device according to claim 8, further comprising:
- a first insulating film arranged between the connecting portions and the corresponding detection electrodes in the normal direction of the substrate; and
- a second insulating film arranged between the connecting portions and the corresponding electrode portions, wherein
- the second insulating film is thinner than the first insulating film.

11. The fingerprint detection device according to claim 7, wherein
- the electrode portions are translucent electrodes, and
- the detection electrodes are metallic thin lines.

12. The fingerprint detection device according to claim 7, wherein the connecting portions are arranged alternately on one side and the other side relative to a virtual line passing through the center of gravity of the electrode portions in the second direction.

* * * * *